US012768811B2

(12) United States Patent
Ito et al.

(10) Patent No.: US 12,768,811 B2
(45) Date of Patent: Oct. 20, 2026

(54) GAS SENSOR

(71) Applicant: NGK INSULATORS, LTD., Nagoya (JP)

(72) Inventors: Yuta Ito, Nagoya (JP); Yusuke Fujii, Nagoya (JP); Akari Yamada, Nagoya (JP)

(73) Assignee: NGK INSULATORS, LTD., Nagoya (JP)

(*) Notice: Subject to any disclaimer, the term of this patent is extended or adjusted under 35 U.S.C. 154(b) by 4 days.

(21) Appl. No.: 18/890,335

(22) Filed: Sep. 19, 2024

(65) Prior Publication Data

US 2025/0110077 A1 Apr. 3, 2025

(30) Foreign Application Priority Data

Sep. 29, 2023 (JP) ................................ 2023-169456

(51) Int. Cl.
*G01N 27/407* (2006.01)
*G01N 33/00* (2006.01)

(52) U.S. Cl.
CPC ..... *G01N 27/4077* (2013.01); *G01N 33/0037* (2013.01)

(58) Field of Classification Search
CPC ............ G01N 27/4077; G01N 27/406; G01N 27/407; G01N 27/4072; G01N 27/4071; G01N 27/4073; G01N 27/4074; G01N 27/4178; G01N 27/4114; G01N 33/0037
See application file for complete search history.

(56) References Cited

U.S. PATENT DOCUMENTS

| | | | |
|---|---|---|---|
| 6,348,141 | B1 | 2/2002 | Kato et al. |
| 6,948,353 | B2 | 9/2005 | Toguchi et al. |
| 7,390,385 | B2 | 6/2008 | Ikoma et al. |
| 10,048,097 | B2 | 8/2018 | Seimori et al. |
| 2005/0016849 | A1 | 1/2005 | Ikoma et al. |
| 2007/0261473 | A1 | 11/2007 | Weyl et al. |

(Continued)

FOREIGN PATENT DOCUMENTS

| | | | |
|---|---|---|---|
| JP | 3829026 | B2 | 10/2006 |
| JP | 4174004 | B2 | 10/2008 |

(Continued)

OTHER PUBLICATIONS

First Examination Report dated Aug. 10, 2026 for Indian Patent Application No. 202444069343.

*Primary Examiner* — Gurpreet Kaur
(74) *Attorney, Agent, or Firm* — MATTINGLY & MALUR, PC

(57) ABSTRACT

A gas sensor includes a sensor element, and a protection cover accommodating a part of the sensor element that includes one end in a longitudinal direction. When a length in the longitudinal direction from the one end of the sensor element to a middle point of a gas inflow hole of the protection cover is represented as La, and a length index between the sensor element and a circle determined by an inner surface of the protection cover is represented as Lb, a ratio La/Lb is 0.9 or more, and, when sum of respective surface areas of two principal surfaces and two side surfaces of the sensor element corresponding to a portion of the length La is represented as S, and a volume of space in the protection cover existing corresponding to the portion of the length La is represented as V, a ratio S/V is 0.15 $mm^{-1}$ or more.

7 Claims, 8 Drawing Sheets

(56) References Cited

U.S. PATENT DOCUMENTS

| | | | |
|---|---|---|---|
| 2019/0277795 | A1 | 9/2019 | Okamoto |
| 2021/0293743 | A1 | 9/2021 | Ichikawa et al. |

FOREIGN PATENT DOCUMENTS

| | | | |
|---|---|---|---|
| JP | 4571974 | B2 | 10/2010 |
| JP | 2021-148656 | A | 9/2021 |
| JP | 6998802 | B2 | 2/2022 |

$$Lb=(x1 + x2 + y1 + y2)/4$$

Fig. 7

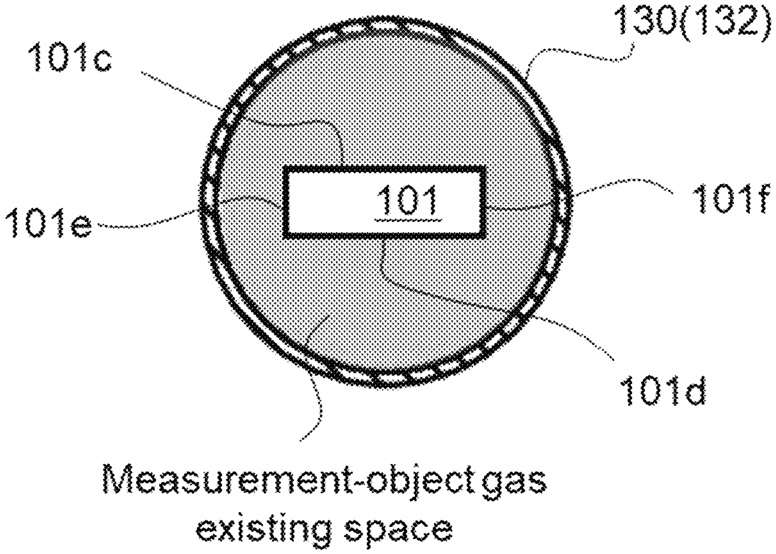

Surface area S [mm$^2$]
= Sum of respective areas of principle surfaces 101c, 101d, and side surfaces 101e, 101f corresponding to portion of length La from element front end surface 101a.

Volume V [mm$^3$]
= Volume of measurement-object gas existing space in inner protection cover 130 corresponding to portion of length La from element front end surface 101a (namely, volume of shaded portion in figure).

GAS SENSOR

CROSS-REFERENCE TO RELATED APPLICATION

The present application claims priority from Japanese Patent Application No. 2023-169456, filed on Sep. 29, 2023, the content of which is hereby incorporated by reference into this application.

BACKGROUND OF THE INVENTION

Technical Field of the Invention

The present invention relates to a gas sensor for detecting a target gas to be measured in a measurement-object gas.

Background Art

A gas sensor is used for detection or measurement of concentration of an objective gas component (oxygen $O_2$, nitrogen oxide NOx, ammonia $NH_3$, hydrocarbon HC, carbon dioxide $CO_2$, etc.) in a measurement-object gas, such as exhaust gas of automobile. For example, a gas sensor is installed on an exhaust passage of a gasoline vehicle or a diesel vehicle, and is used for measuring a concentration of nitrogen oxide NOx, ammonia $NH_3$, or the like in exhaust gas.

As such a gas sensor, a gas sensor which has a sensor element using an oxygen ion conductive solid electrolyte such as zirconia ($ZrO_2$), and protective cover protecting a portion of the sensor element which is in contact with a measurement-object gas is known. In such a gas sensor, protective covers of various structures are used in accordance with various purposes such as reduction in attachment of water to the sensor element, and reduction in temperature change of the sensor element due to the measurement-object gas (for example, JP 3829026 B, JP 4174004 B, JP 6998802 B, JP 2021-148656 A, and JP 4571974 B).

CITATION LIST

Patent Documents

Patent Document 1: JP 3829026 B
Patent Document 2: JP 4174004 B
Patent Document 3: JP 6998802 B
Patent Document 4: JP 2021-148656 A
Patent Document 5: JP 4571974 B

SUMMARY OF THE INVENTION

Problems to be Solved by the Invention

Measurement of concentration of nitrogen oxide NOx, ammonia $NH_3$, or the like in the exhaust gas is required not only for a gasoline vehicle and a diesel vehicle but also for a hydrogen engine vehicle.

In an exhaust path of the hydrogen engine vehicle, a gas atmosphere is assumed to contain both of oxygen and hydrogen. It is widely known that hydrogen explosion can be occurred when oxygen and hydrogen are within a certain concentration range, and that hydrogen ignites spontaneously at high temperature of 500° C. or more in the air.

When a gas sensor as described above is used in the exhaust path of the hydrogen engine vehicle, oxygen and hydrogen may react rapidly in the gas sensor and thermal stress caused by the reaction heat may generate a crack in an internal structure of a sensor element, depending on a gas atmosphere (especially, oxygen concentration and hydrogen concentration), and operation conditions of the gas sensor such as temperature.

It is therefore an object of the present invention to provide a gas sensor that can accurately measure a target gas to be measured in a measurement-object gas by suppressing the occurrence of cracking in a sensor element even when a gas containing gas species that can cause an exothermic reaction, such as a gas in which oxygen and hydrogen coexist, is introduced into the gas sensor as the measurement-object gas.

Means for Solving the Problems

The present inventors have intensively studied and found that the occurrence of cracking in a sensor element can be suppressed even when the gas containing gas species that can cause an exothermic reaction is introduced into the gas sensor as the measurement-object gas, by determining positional relation between the sensor element and a gas inflow hole provided on a protection cover accommodating a part of the sensor element.

The present invention includes the following aspects.

(1) A gas sensor for detecting a target gas to be measured in a measurement-object gas, the gas sensor comprising:

a sensor element in an elongated plate shape, including an oxygen-ion-conductive solid electrolyte layer, wherein a measurement-object gas flow cavity is formed on a side of one end in a longitudinal direction of the sensor element; and a protection cover in a bottomed cylindrical shape, accommodating a part of the sensor element that includes the one end in the longitudinal direction of the sensor element, wherein the protection cover has a gas inflow hole penetrating a side surface of the protection cover that surrounds the sensor element, and when a length in the longitudinal direction of the sensor element from the one end of the sensor element to a middle point in the longitudinal direction of the gas inflow hole of the protection cover is represented as a length La, and in a plane including the middle point in the longitudinal direction of the gas inflow hole of the protection cover and perpendicular to the longitudinal direction of the sensor element, a longest distance between each of two principal surfaces of the sensor element and circumference of a circle determined by an inner surface of the protection cover facing the each of the two principal surfaces is represented as a length x1 or a length x2, a longest distance between each of two side surfaces of the sensor element and circumference of the circle facing the each of the two side surfaces is represented as a length y1 or a length y2, and an index of a length between the sensor element and the circle determined by the inner surface of the protection cover is represented as a length index:

$$Lb = (x1 + x2 + y1 + y2)/4,$$

a ratio La/Lb of the length La to the length index Lb is 0.9 or more, and when sum of respective surface areas of the two principal surfaces and the two side surfaces of the sensor element corresponding to a portion of the length La in the longitudinal direction is represented as a surface area S, and a volume of space in the protection cover existing corresponding to the portion of the length La in the longitudinal direction is represented as a volume V, a ratio S/V of the surface area S to the volume V is 0.15 $mm^{-1}$ or more.

(2) The gas sensor according to the above (1), wherein the length La in the longitudinal direction is 10 mm or less.

(3) The gas sensor according to the above (1) or (2), wherein the length x1 and the length x2 are x1=x2=x, the length y1 and the length y2 are y1=y2=y, and the length index Lb is represented as Lb=(x+y)/2.

The above (3) intends the case that the sensor element is arranged at a center of the protection cover in the plane including the middle point in the longitudinal direction of the gas inflow hole and perpendicular to the longitudinal direction of the sensor element.

(4) The gas sensor according to any one of the above (1) to (3), wherein the protection cover has a gas outflow hole on a bottom of the protection cover.

(5) The gas sensor according to any one of the above (1) to (4), wherein an outer cover is further disposed outside the protection cover and accommodates the protection cover, and the outer cover has an outer gas inflow hole at a position different from the gas inflow hole of the protection cover in the longitudinal direction of the sensor element.

(6) The gas sensor according to the above (5), wherein the outer cover has an outer gas outflow hole at a position different from the gas inflow hole of the protection cover and the outer gas inflow hole of the outer cover in the longitudinal direction of the sensor element.

(7) The gas sensor according to any one of the above (1) to (6), wherein the measurement-object gas flow cavity of the sensor element has a gas inlet that is open to an end surface of the one end in the longitudinal direction of the sensor element.

Advantageous Effect of the Invention

According to the present invention, it is possible to provide a gas sensor that can accurately measure a target gas to be measured in a measurement-object gas by suppressing the occurrence of cracking in a sensor element even when a gas containing gas species that can cause an exothermic reaction, such as a gas in which oxygen and hydrogen coexist, is introduced into the gas sensor as the measurement-object gas.

BRIEF DESCRIPTION OF THE DRAWINGS

In FIG. 5, illustration of an outer protection cover 140 is omitted.

FIG. 7 is an enlarged partial sectional schematic view along a line VII-VII in FIG. 6, for illustrating a surface area S and the volume V.

MODES FOR CARRYING OUT OF THE INVENTION

A gas sensor of the present invention includes a sensor element, and a protection cover in a bottomed cylindrical shape, accommodating a part of the sensor element that includes one end in the longitudinal direction of the sensor element.

The sensor element contained in the gas sensor of the present invention is in an elongated plate shape, including an oxygen-ion-conductive solid electrolyte layer, and wherein a measurement-object gas flow cavity is formed on a side of the one end in a longitudinal direction of the sensor element.

The protection cover contained in the gas sensor of the present invention is a cover in a bottomed cylindrical shape, accommodating a part of the sensor element that includes the one end of the sensor element where the measurement-object gas flow cavity is formed. The protection cover has a gas inflow hole penetrating a side surface of the protection cover that surrounds the sensor element.

In the gas sensor of the present invention, when a length in the longitudinal direction of the sensor element from the one end of the sensor element to a middle point in the longitudinal direction of the gas inflow hole of the protection cover is represented as a length La, and in a plane including the middle point in the longitudinal direction of the gas inflow hole of the protection cover and perpendicular to the longitudinal direction of the sensor element, a longest distance between each of two principal surfaces of the sensor element and circumference of a circle determined by an inner surface of the protection cover facing the each of the two principal surfaces is represented as a length x1 or a length x2, a longest distance between each of two side surfaces of the sensor element and circumference of the circle facing the each of the two side surfaces is represented as a length y1 or a length y2, and an index of a length between the sensor element and the circle determined by the inner surface of the protection cover is represented as a length index:

$$Lb=(x1+x2+y1+y2)/4,$$

a ratio La/Lb of the length La to the length index Lb is 0.9 or more, and when sum of respective surface areas of the two principal surfaces and the two side surfaces of the sensor element corresponding to a portion of the length La in the longitudinal direction is represented as a surface area S, and a volume of space in the protection cover existing corresponding to the portion of the length La in the longitudinal direction is represented as a volume V, a ratio S/V of the surface area S to the volume V is 0.15 $mm^{-1}$ or more.

[Schematic Configuration of Gas Sensor]

Figure 1:
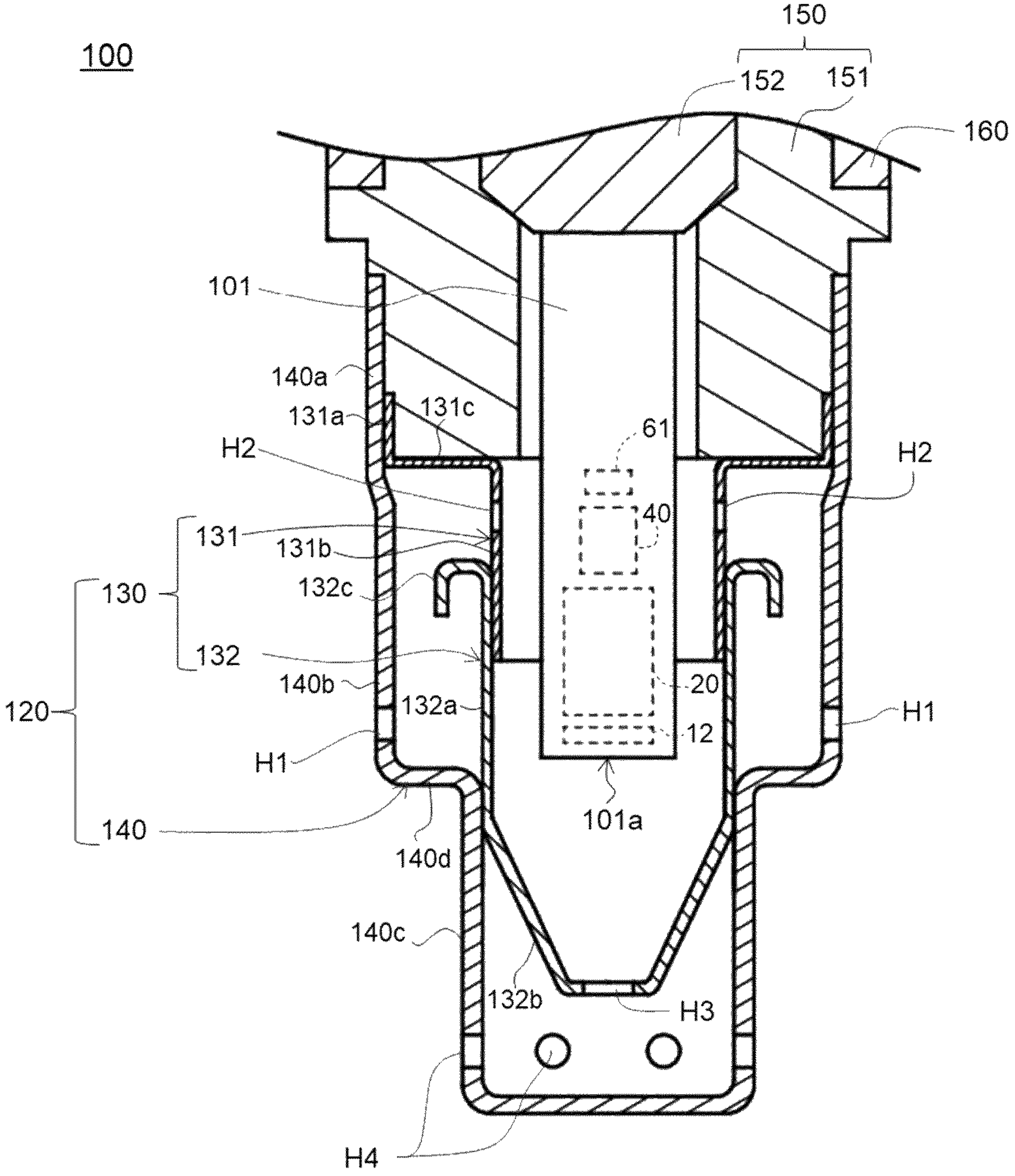
FIG. 1 is a partial sectional schematic view, showing one example of schematic configuration of a gas sensor 100.
Figure 2:
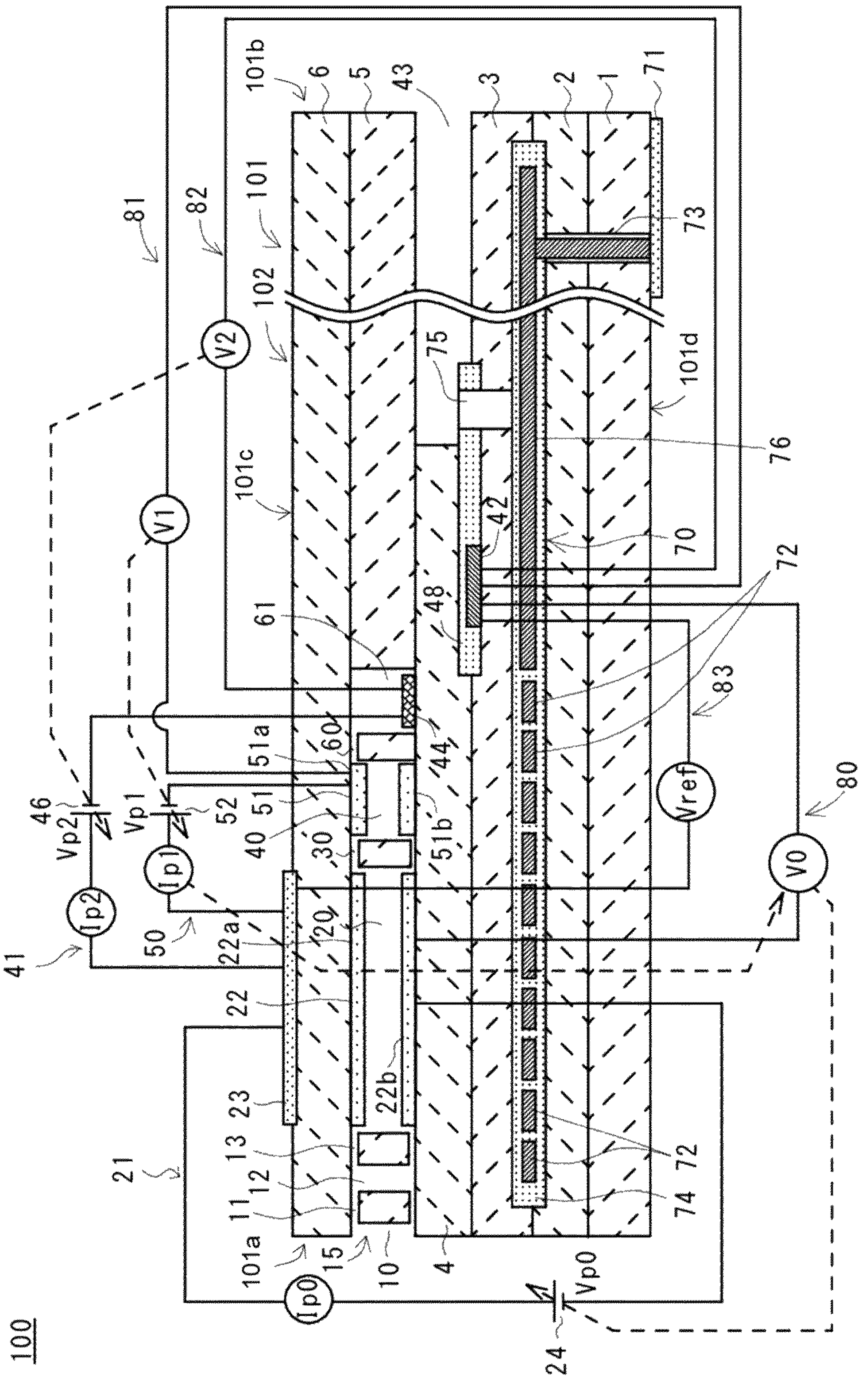
FIG. 2 is a vertical sectional schematic view in the longitudinal direction of a sensor element 101, showing one example of the schematic configuration of the gas sensor 100.

The gas sensor of the present invention will now be described with reference to the drawings. FIG. 1 is a partial sectional schematic view, showing one example of schematic configuration of a gas sensor 100 which is one embodiment of the present invention. FIG. 2 is a vertical sectional schematic view in the longitudinal direction of a sensor element 101, showing one example of the schematic configuration of the gas sensor 100. Internal structure of the sensor element 101 is illustrated in detain in FIG. 2, while illustrations of the internal structure of the sensor element 101 are omitted in FIG. 1 with some exceptions. Hereinafter, based on FIG. 2, the upper side and the lower side in FIG. 2 are respectively defined as top and bottom, and the left side and the right side in FIG. 2 are respectively defined as a front end side and a rear end side. And, based on FIG. 2, the front side and the back side perpendicular to the paper are respectively defined as a right side and a left side. The front side and the back side perpendicular to the paper of FIG. 1 respectively correspond to the top and the bottom defined based on FIG. 2. And, the lower side, upper side, right side, and left side of FIG. 1 respectively correspond to the front end side, the rear end side, the right side and the left side defined based on FIG. 2.

As shown in FIG. 1, the gas sensor 100 includes a sensor element 101, and an element protection cover 120 to protect the front end side of the sensor element 101. The gas sensor 100 also includes an element scaling body 150 to seal and fix the sensor element 101, and a fixing part 160 attached to the element sealing body 150. For example, this gas sensor 100 is attached to a pipe such as an exhaust gas pipe of a vehicle and used to measure the concentration of a target gas to be measured, such as NOx, $NH_3$, and $O_2$ contained in exhaust gas as a measurement-object gas. In the present embodiment, the gas sensor 100 measures the concentration of NOx as a target gas to be measured.

The element sealing body 150 includes a cylindrical metal housing 151, and a ceramic supporter 152 encapsulated in a through-hole inside the housing 151. The sensor element 101 is located on a central axis of the element scaling body 150 and extends through the element scaling body 150 in the front and rear direction. On the rear end side of the sensor element 101 rather than the ceramic supporter 152 in the through-hole inside the housing 151, a green compact (not shown) composed of a ceramic powder such as talc, and at least one ceramic supporter (not shown) are located. The green compact sandwiched between ceramic supporters seals the through-hole inside the housing 151 to ensure gastightness between the front end side and the rear end side of the sensor element 101, and fixes the sensor element 101.

The fixing part 160 is a metal member in a doughnut shape. The fixing part 160 is concentrically fixed to the housing 151 and has an external thread (not shown) formed on an outer peripheral surface thereof. The gas sensor 100 is screwed on the pipe by the fixing part 160. The fixing part 160 may configured that fixing by welding or the like is conducted. The fixing part 160 may be integrally formed with the element scaling body 150. The gas sensor 100 is fixed to the pipe by the fixing part 160 in a state where a of the gas sensor 100 such as the front end of the sensor element 101 and the element protection cover 120 protrudes into the pipe.

The rear end of the sensor element 101 is accommodated in a metal-made external cylinder (not shown). The space inside the outer cylinder is filled with a reference gas (for example, air) for NOx concentration measurement, and the rear end of the sensor element 101 is to be in contact with the reference gas. Each of electrodes of the sensor element 101 is electrically connected to the outside (i.e., a power supply and a control unit) via a connector disposed on the rear end portion of the sensor element 101.

The element protection cover 120 includes a bottomed cylindrical inner protection cover 130 to accommodate a part of the sensor element 101 including the front end, and a bottomed cylindrical outer protection cover 140 to accommodate the inner protection cover 130. The element protection cover 120 has a plurality of penetrating holes to flow a gas, and is configured to supply a measurement-object gas to the front end side of the sensor element 101 through the penetrating holes. Details of the element protection cover 120 will be described later.

(Sensor Element)

As shown in FIG. 2, the sensor element 101 is an element in an elongated plate shape, including a base part 102 having such a structure that a plurality of oxygen-ion-conductive solid electrolyte layers are layered. The elongated plate shape also called a long plate shape or a belt shape. The base part 102 has such a structure that six layers, namely, a first substrate layer 1, a second substrate layer 2, a third substrate layer 3, a first solid electrolyte layer 4, a spacer layer 5, and a second solid electrolyte layer 6, are layered in this order from the bottom side, as viewed in the drawing. Each of the six layers is formed of an oxygen-ion-conductive solid electrolyte layer containing, for example, zirconia ($ZrO_2$). The solid electrolyte forming these six layers is dense and gastight. These six layers all may have the same thickness, or the thickness may vary among the layers. The layers are adhered to each other with an adhesive layer of a solid electrolyte interposed therebetween, and the base part 102 includes the adhesive layer. While a layer configuration composed of the six layers is illustrated in FIG. 2, the layer configuration in the present invention is not limited to this, and any number of layers and any layer configuration are possible.

The sensor element 101 is manufactured, for example, by stacking ceramic green sheets corresponding to the individual layers after conducting predetermined processing, printing of circuit pattern and the like, and then firing the stacked ceramic green sheets so that they are combined together.

The sensor element 101 has an elongated plate shape, and has six surfaces including two end surfaces in the longitudinal direction (a front end surface 101*a* and a rear end surface 101*b*), two principal surfaces along the longitudinal direction (a top surface 101*c* and a bottom surface 101*d*), and two side surfaces along the longitudinal direction (a left surface 101*e* and a right surface 101*f*). In FIG. 2, the left surface 101*e* and the right surface 101*f* are not shown.

On a side of the one end of the sensor element 101, a measurement-object gas flow cavity 15 is formed. Hereinafter, one end where the measurement-object gas flow cavity 15 is formed is referred to as a front end. In this embodiment, a gas inlet 10 is open to the front end surface 101*a* of the sensor element 101, and a measurement-object gas is introduced into the measurement-object gas flow cavity 15 inside the sensor element 101 from the gas inlet 10.

Specifically, the gas inlet 10 is formed between the lower surface of the second solid electrolyte layer 6 and the upper surface of the first solid electrolyte layer 4 in a front end part in the longitudinal direction of the sensor element 101. The measurement-object gas flow cavity 15, that is, a measurement-object gas flow part is formed in such a form that a first diffusion-rate limiting part 11, a buffer space 12, a second diffusion-rate limiting part 13, a first internal cavity 20, a third diffusion-rate limiting part 30, a second internal cavity 40, a fourth diffusion-rate limiting part 60, and a third internal cavity 61 communicate in this order in the longitudinal direction from the gas inlet 10.

The gas inlet 10, the buffer space 12, the first internal cavity 20, the second internal cavity 40, and the third internal cavity 61 constitute internal spaces of the sensor element 101. Each of the internal spaces is provided in such a manner that a portion of the spacer layer 5 is hollowed out, and the top of each of the internal spaces is defined by the lower surface of the second solid electrolyte layer 6, the bottom of each of the internal spaces is defined by the upper surface of the first solid electrolyte layer 4, and the lateral surface of each of the internal spaces is defined by the lateral surface of the spacer layer 5.

Each of the first diffusion-rate limiting part 11, the second diffusion-rate limiting part 13, and the third diffusion-rate limiting part 30 is provided as two laterally elongated slits (having the longitudinal direction of the openings in the direction perpendicular to the figure in FIG. 2). Each of the first diffusion-rate limiting part 11, the second diffusion-rate limiting part 13, and the third diffusion-rate limiting part 30 may be in such a form that a desired diffusion resistance is created, but the form is not limited to the slits.

The fourth diffusion-rate limiting part 60 is provided as a single laterally elongated slit (having the longitudinal direction of the opening in the direction perpendicular to the figure in FIG. 2) between the spacer layer 5 and the second solid electrolyte layer 6. The fourth diffusion-rate limiting part 60 may be in such a form that a desired diffusion resistance is created, but the form is not limited to the slit.

Also, at a position farther from the front end than the measurement-object gas flow cavity 15, a reference gas introduction space 43 is disposed between the upper surface of the third substrate layer 3 and the lower surface of the spacer layer 5 at a position where the reference gas introduction space 43 is laterally defined by the lateral surface of the first solid electrolyte layer 4. The reference gas introduction space 43 has an opening in the other end part (hereinafter, referred to as a rear end part) of the sensor element 101. As a reference gas for NOx concentration measurement, for example, air is introduced into the reference gas introduction space 43.

An air introduction layer 48 is a layer formed of porous alumina, and is so configured that a reference gas is introduced into the air introduction layer 48 via the reference gas introduction space 43. The air introduction layer 48 is formed to cover a reference electrode 42.

The reference electrode 42 is an electrode sandwiched between the upper surface of the third substrate layer 3 and the first solid electrolyte layer 4, and as described above, the air introduction layer 48 leading to the reference gas introduction space 43 is disposed around the reference electrode 42. That is, the reference electrode 42 is disposed to be in contact with a reference gas via the air introduction layer 48 which is a porous material, and the reference gas introduction space 43. As will be described later, the reference electrode 42 can be used to measure the oxygen concentration (oxygen partial pressure) in the first internal cavity 20, the second internal cavity 40, and the third internal cavity 61. The reference electrode 42 is formed as a porous cermet electrode (e.g., a cermet electrode of Pt and $ZrO_2$).

In the measurement-object gas flow cavity 15, the gas inlet 10 is open to the external space, and the measurement-object gas is taken into the sensor element 101 from the external space through the gas inlet 10.

In the present embodiment, the measurement-object gas flow cavity 15 is in such a form that the measurement-object gas is introduced through the gas inlet 10 that is open on the front end surface of the sensor element 101, however, the present invention is not limited to this form. For example, the measurement-object gas flow cavity 15 need not have a recess of the gas inlet 10. In this case, the first diffusion-rate limiting part 11 substantially serves as a gas inlet.

Further, for example, the measurement-object gas flow cavity 15 may be so configured that the measurement-object gas is introduced through a porous body.

The first diffusion-rate limiting part 11 creates a predetermined diffusion resistance to the measurement-object gas taken through the gas inlet 10.

The buffer space 12 is provided to guide the measurement-object gas introduced from the first diffusion-rate limiting part 11 to the second diffusion-rate limiting part 13.

The second diffusion-rate limiting part 13 creates a predetermined diffusion resistance to the measurement-object gas introduced into the first internal cavity 20 from the buffer space 12.

It suffices that the amount of the measurement-object gas to be introduced into the first internal cavity 20 finally falls within a predetermined range. That is, it suffices that a predetermined diffusion resistance is created in a whole from the front end part of the sensor element 101 to the second diffusion-rate limiting part 13. For example, the first diffusion-rate limiting part 11 may directly communicate with the first internal cavity 20, or the buffer space 12 and the second diffusion-rate limiting part 13 may be absent.

The buffer space 12 is provided to mitigate the influence of pressure fluctuation on the detected value when the pressure of the measurement-object gas fluctuates.

When the measurement-object gas is introduced from outside the sensor element 101 into the first internal cavity 20, the measurement-object gas, which is rapidly taken through the gas inlet 10 into the sensor element 101 due to pressure fluctuation of the measurement-object gas in the external space (pulsations in exhaust pressure if the measurement-object gas is automotive exhaust gas), is not directly introduced into the first internal cavity 20. Rather, the measurement-object gas is introduced into the first internal cavity 20 after the pressure fluctuation of the measurement-object gas is eliminated through the first diffusion-rate limiting part 11, the buffer space 12, and the second diffusion-rate limiting part 13. Thus, the pressure fluctuation of the measurement-object gas introduced into the first internal cavity 20 becomes almost negligible.

The first internal cavity 20 is provided as a space for adjusting the oxygen partial pressure in the measurement-object gas introduced through the second diffusion-rate limiting part 13. The oxygen partial pressure is adjusted by operation of a main pump cell 21.

The main pump cell 21 is an electrochemical pump cell composed of an inner main pump electrode 22 having a ceiling electrode portion 22*a* disposed over substantially the entire surface of the lower surface of the second solid electrolyte layer 6 that faces the first internal cavity 20, an outer pump electrode 23 disposed on a region of the upper surface of the second solid electrolyte layer 6 that corresponds to the ceiling electrode portion 22*a* so as to be exposed to the external space, and the second solid electrolyte layer 6 sandwiched between the inner main pump electrode 22 and the outer pump electrode 23.

The inner main pump electrode 22 is disposed facing the first internal cavity 20 on an inner surface of the measurement-object gas flow cavity 15. That is, the inner main pump electrode 22 is formed to span the upper and lower solid electrolyte layers (the second solid electrolyte layer 6 and the first solid electrolyte layer 4) that define the first internal cavity 20 and the spacer layer 5 that defines the lateral wall. Specifically, the ceiling electrode portion 22*a* is formed on the lower surface of the second solid electrolyte layer 6 that defines the ceiling surface of the first internal cavity 20, and a bottom electrode portion 22*b* is formed on the upper surface of the first solid electrolyte layer 4 that defines the bottom surface of the first internal cavity 20. Also, lateral electrode portions (not shown) are formed on the lateral wall surfaces (inner surface) of the spacer layer 5 that form both lateral wall parts of the first internal cavity 20 so as to connect the ceiling electrode portion 22*a* and the bottom electrode portion 22*b*. Thus, the inner main pump electrode 22 is provided as a tunnel-like structure in the area where the lateral electrode portions are disposed.

The inner main pump electrode 22 and the outer pump electrode 23 are each formed as a porous cermet electrode (e.g., a cermet electrode of Pt containing 1% Au and $ZrO_2$). It is to be noted that the inner main pump electrode 22 to be in contact with the measurement-object gas is formed using a material having a weakened ability to reduce a NOx component in the measurement-object gas.

In the main pump cell 21, a desired pump voltage Vp0 is applied between the inner main pump electrode 22 and the outer pump electrode 23 by a variable power supply 24 to flow a pump current Ip0 between the inner main pump electrode 22 and the outer pump electrode 23 in either a positive or negative direction, and thus it is possible to pump out oxygen in the first internal cavity 20 to the external space or pump oxygen into the first internal cavity 20 from the external space.

To detect the oxygen concentration (oxygen partial pressure) in the atmosphere in the first internal cavity 20, the inner main pump electrode 22, the second solid electrolyte layer 6, the spacer layer 5, the first solid electrolyte layer 4, the third substrate layer 3, and the reference electrode 42 form an electrochemical sensor cell, namely, an oxygen-partial-pressure detection sensor cell 80 for main pump control.

The oxygen concentration (oxygen partial pressure) in the first internal cavity 20 can be detected from an electromotive force (a voltage V0) measured in the oxygen-partial-pressure detection sensor cell 80 for main pump control. In addition, the pump current Ip0 is controlled by performing feedback control of the pump voltage Vp0 so that the electromotive force V0 is constant. Thus, the oxygen concentration in the first internal cavity 20 can be maintained at a predetermined constant value.

The third diffusion-rate limiting part 30 creates a predetermined diffusion resistance to the measurement-object gas whose oxygen concentration (oxygen partial pressure) has been controlled in the first internal cavity 20 by the operation of the main pump cell 21, and guides the measurement-object gas into the second internal cavity 40.

The second internal cavity 40 is provided as a space for adjusting the oxygen partial pressure in the measurement-object gas introduced through the third diffusion-rate limiting part 30 more accurately. The oxygen partial pressure is adjusted by operation of an auxiliary pump cell 50.

After the oxygen concentration (oxygen partial pressure) in the measurement-object gas is adjusted in advance in the first internal cavity 20, the measurement-object gas is introduced through the third diffusion-rate limiting part 30, and is further subjected to adjustment of the oxygen partial pressure by the auxiliary pump cell 50 in the second internal cavity 40. Thus, the oxygen concentration in the second internal cavity 40 can be kept constant with high accuracy, and the NOx concentration can be measured with high accuracy in the gas sensor 100.

The auxiliary pump cell 50 is an auxiliary electrochemical pump cell composed of an auxiliary pump electrode 51 having a ceiling electrode portion 51*a* disposed on substantially the entire surface of the lower surface of the second solid electrolyte layer 6 facing with the second internal cavity 40, the outer pump electrode 23 (the outer electrode is not limited to the outer pump electrode 23, but may be any suitable electrode at a position different from the measurement-object gas flow cavity 15, for example, outside the sensor element 101), and the second solid electrolyte layer 6.

The auxiliary pump electrode 51 is disposed at a position farther from the one end part (front end part) of the base part 102 (sensor element 101) than the inner main pump electrode 22 on the inner surface of the measurement-object gas flow cavity 15.

The auxiliary pump electrode 51 is disposed in the second internal cavity 40 in a tunnel-like structure similar to the inner main pump electrode 22 disposed in the first internal cavity 20. Specifically, in the tunnel-like structure, the ceiling electrode portion 51*a* is formed on the second solid electrolyte layer 6 that defines the ceiling surface of the second internal cavity 40, a bottom electrode portion 51*b* is formed on the first solid electrolyte layer 4 that defines the bottom surface of the second internal cavity 40, and lateral electrode portions (not shown) connecting the ceiling electrode portion 51*a* and the bottom electrode portion 51*b* are formed on the wall surfaces of the spacer layer 5 that define the lateral walls of the second internal cavity 40.

It is to be noted that the auxiliary pump electrode 51 is formed using a material having a weakened ability to reduce a NOx component in the measurement-object gas, as with the case of the inner main pump electrode 22.

In the auxiliary pump cell 50, by applying a desired voltage Vp1 between the auxiliary pump electrode 51 and the outer pump electrode 23 by a variable power supply 52, it is possible to pump out oxygen in the atmosphere in the second internal cavity 40 to the external space, or pump the oxygen into the second internal cavity 40 from the external space.

To control the oxygen partial pressure in the atmosphere in the second internal cavity 40, the auxiliary pump electrode 51, the reference electrode 42, the second solid electrolyte layer 6, the spacer layer 5, the first solid electrolyte layer 4, and the third substrate layer 3 constitute an electrochemical sensor cell, namely, an oxygen-partial-pressure detection sensor cell 81 for auxiliary pump control.

The auxiliary pump cell 50 performs pumping with the variable power supply 52 whose voltage is controlled on the basis of an electromotive force (a voltage V1) detected by the oxygen-partial-pressure detection sensor cell 81 for auxiliary pump control. Thus, the oxygen partial pressure in the atmosphere in the second internal cavity 40 is controlled to such a low partial pressure that does not substantially affect measurement of NOx.

In addition, a pump current Ip1 of the auxiliary pump cell 50 is used for control of the voltage V0 of the oxygen-partial-pressure detection sensor cell 80 for main pump control. Specifically, the pump current Ip1 is input to the oxygen-partial-pressure detection sensor cell 80 for main pump control as a control signal to control the voltage V0, and thus the gradient of the oxygen partial pressure in the measurement-object gas introduced into the second internal cavity 40 from the third diffusion-rate limiting part 30 is controlled to remain constant. In using as a NOx sensor, the oxygen concentration in the second internal cavity 40 is kept at a constant value of about 0.001 ppm by the actions of the main pump cell 21 and the auxiliary pump cell 50.

The fourth diffusion-rate limiting part 60 creates a predetermined diffusion resistance to the measurement-object gas whose oxygen concentration (oxygen partial pressure) has been controlled to further low in the second internal cavity 40 by the operation of the auxiliary pump cell 50, and guides the measurement-object gas into the third internal cavity 61.

The third internal cavity 61 is provided as a space for measuring nitrogen oxide (NOx) concentration in the measurement-object gas introduced through the fourth diffusion-rate limiting part 60. By the operation of a measurement pump cell 41, NOx concentration is measured.

The measurement pump cell 41 measures NOx concentration in the measurement-object gas in the third internal cavity 61. The measurement pump cell includes an inner measurement electrode (in this embodiment, a measurement electrode 44) disposed in the measurement-object gas flow cavity 15 (on the inner surface of the measurement-object gas flow cavity 15), and an outer measurement electrode (in this embodiment, the outer pump electrode 23) disposed at a position different from the measurement-object gas flow cavity 15 on the base part 102 and corresponding to the inner measurement electrode.

That is, in this embodiment, the measurement pump cell 41 is an electrochemical pump cell composed of the measurement electrode 44 disposed on the upper surface of the first solid electrolyte layer 4 facing with the third internal cavity 61, the outer pump electrode 23 (the outer electrode is not limited to the outer pump electrode 23, but may be any suitable electrode at a position different from the measurement-object gas flow cavity 15, for example, outside the sensor element 101), the second solid electrolyte layer 6, the spacer layer 5, and the first solid electrolyte layer 4.

The measurement electrode 44 is disposed at a position farther from the one end part (front end part) in the longitudinal direction of the base part 102 (sensor element 101) than the inner main pump electrode 22 and the auxiliary pump electrode 51 on the inner surface of the measurement-object gas flow cavity 15.

The measurement electrode 44 is a porous cermet electrode. The measurement electrode 44 functions also as a NOx reduction catalyst that reduces NOx present in the atmosphere in the third internal cavity 61. For example, in this embodiment, the measurement electrode 44 is formed as a porous cermet electrode made of Pt and Rh, and $ZrO_2$.

In the measurement pump cell 41, oxygen generated by decomposition of nitrogen oxide in the atmosphere around the measurement electrode 44 is pumped out, and the amount of generated oxygen can be detected as a pump current Ip2.

To detect the oxygen partial pressure around the measurement electrode 44, the first solid electrolyte layer 4, the third substrate layer 3, the measurement electrode 44, and the reference electrode 42 constitute an electrochemical sensor cell, namely an oxygen-partial-pressure detection sensor cell 82 for measurement pump control. A variable power supply 46 is controlled on the basis of an electromotive force (a voltage V2) detected by the oxygen-partial-pressure detection sensor cell 82 for measurement pump control.

The measurement-object gas introduced into the second internal cavity 40 reaches the measurement electrode 44 in the third internal cavity 61 through the fourth diffusion-rate limiting part 60 under the condition that the oxygen partial pressure is controlled. Nitrogen oxide in the measurement-object gas around the measurement electrode 44 is reduced ($2NO \rightarrow N_2+O_2$) to generate oxygen. The generated oxygen is to be pumped by the measurement pump cell 41, and at this time, a pump voltage Vp2 of the variable power supply 46 is controlled so that the voltage V2 detected by the oxygen-partial-pressure detection sensor cell 82 for measurement pump control is constant. Since the amount of oxygen generated around the measurement electrode 44 is proportional to the concentration of nitrogen oxide in the measurement-object gas, nitrogen oxide concentration in the measurement-object gas is calculated by using the pump current Ip2 in the measurement pump cell 41.

By configuring oxygen partial pressure detecting means by an electrochemical sensor cell composed of a combination of the measurement electrode 44, the first solid electrolyte layer 4, the third substrate layer 3 and the reference electrode 42, it is possible to detect an electromotive force in accordance with a difference between the amount of oxygen generated by reduction of NOx components in the atmosphere around the measurement electrode 44 and the amount of oxygen contained in the reference air, and hence it is possible to determine the concentration of NOx components in the measurement-object gas.

Also, the second solid electrolyte layer 6, the spacer layer 5, the first solid electrolyte layer 4, the third substrate layer 3, the outer pump electrode 23, and the reference electrode 42 constitute an electrochemical sensor cell 83, and it is possible to detect the oxygen partial pressure in the measurement-object gas outside the sensor by an electromotive force Vref obtained by the sensor cell 83.

In the gas sensor 100 having such a configuration, the main pump cell 21 and the auxiliary pump cell 50 are operated to supply a measurement-object gas whose oxygen partial pressure is usually kept at a low constant value (the value that does not substantially affect measurement of NOx) to the measurement pump cell 41. Therefore, NOx concentration in the measurement-object gas can be detected on the basis of the pump current Ip2 that flows as a result of pumping out of the oxygen generated by reduction of NOx by the measurement pump cell 41 and is almost in proportion to the concentration of NOx in the measurement-object gas.

The sensor element 101 further includes a heater part 70 that functions as a temperature regulator of heating and maintaining the temperature of the sensor element 101 so as to enhance the oxygen ion conductivity of the solid electrolyte. The heater part 70 includes a heater electrode 71, a heater 72, a heater lead 76, a through hole 73, a heater insulating layer 74, and a pressure relief vent 75.

The heater electrode 71 is an electrode formed in contact with the lower surface of the first substrate layer 1. The power can be supplied to the heater part 70 from the outside by connecting the heater electrode 71 with a heater power supply that is an external power supply.

The heater 72 is an electrical resistor sandwiched by the second substrate layer 2 and the third substrate layer 3 from top and bottom. The heater 72 is connected with the heater electrode 71 via the heater lead 76 that connects with the heater 72 and extends in the rear end side in the longitudinal direction of the sensor element 101, and the through hole 73. The heater 72 is externally powered through the heater electrode 71 to generate heat, and heats and maintains the temperature of the solid electrolyte forming the sensor element 101.

The heater 72 is embedded over the whole area from the first internal cavity 20 to the third internal cavity 61 so that the temperature of the entire sensor element 101 can be adjusted to such a temperature that activates the solid electrolyte. The temperature may be adjusted so that the main pump cell 21, the auxiliary pump cell 50, and the measurement pump cell 41 are operable. It is not necessary that the whole area is adjusted to the same temperature, but the sensor element 101 may have temperature distribution. For example, the sensor element 101 may be heated so that temperature of the solid electrolyte around the measurement-object gas flow cavity 15 and each of the electrodes become about 750° C. to about 900° C.

In the sensor element 101 of the present embodiment, the heater 72 is embedded in the base part 102, but this form is not limitative. The heater 72 may be disposed to heat the base part 102. That is, the heater 72 may heat the sensor element 101 to develop oxygen ion conductivity with which the main pump cell 21, the auxiliary pump cell 50, and the measurement pump cell 41 are operable. For example, the heater 72 may be embedded in the base part 102 as in the present embodiment. Alternatively, for example, the heater part 70 may be formed as a heater substrate that is separate from the base part 102, and may be disposed at a position adjacent to the base part 102.

The heater insulating layer 74 is formed of an insulator such as alumina on the upper and lower surfaces of the heater 72 and the heater lead 76. The heater insulating layer 74 is formed to ensure electrical insulation between the second substrate layer 2, and the heater 72 and the heater lead 76, and electrical insulation between the third substrate layer 3, and the heater 72 and the heater lead 76.

The pressure relief vent 75 extends through the third substrate layer 3 so that the heater insulating layer 74 and the reference gas introduction space 43 communicate with each other. The pressure relief vent 75 can mitigate an increase in internal pressure due to temperature rise in the heater insulating layer 74. The pressure relief vent 75 may be absent.

Further, an area of a predetermined length in the longitudinal direction in a surface of the sensor element 101 from the front end may be covered by a porous protective layer not shown. The porous protective layer is formed to protect a region where the internal cavities and the electrodes are present in the sensor element 101 from thermal shock caused by water splashing or the like. The porous protective layer may be made of ceramics such alumina, and may have a thickness of approximately 10 μm to 2000 μm. Preferably, the porous protective layer may be formed so as to resist forces up to approximately 50 N.

The above-described sensor element 101 is incorporated into the gas sensor 100 in such a form that the front end part of the sensor element 101 comes into contact with the measurement-object gas, and the rear end part of the sensor element 101 comes into contact with the reference gas. The front end part of the sensor element 101 is accommodated in the internal space of the element protection cover 120, as shown in FIG. 1.

[Use of Gas Sensor Under Condition Where Oxygen and Hydrogen Coexist]

The case of measuring a target gas to be measured (in this embodiment, NOx) in a measurement-object gas in which oxygen and hydrogen coexist is considered. The measurement-object gas includes exhaust gas from an internal combustion engine such as a hydrogen engine and a gasoline engine.

For example, in a hydrogen engine vehicle, an exhaust gas purification device including an oxidation catalyst is usually located in an exhaust pipe downstream of a hydrogen engine, so that hydrogen unburned in the hydrogen engine is oxidized in the oxidation catalyst. However, hydrogen may be discharged downstream of the oxidation catalyst without being oxidized before warm-up of the oxidation catalyst is completed at cold start. At such a time before the warm-up of the oxidation catalyst is completed at the cold start, hydrogen may reach the gas sensor 100 without being oxidized in the oxidation catalyst even when the gas sensor 100 is used by mounting the exhaust pipe downstream of the oxidation catalyst.

In use of the gas sensor 100, as described above, the sensor element 101 is heated by the heater 72 and the front end part of the sensor element 101 in which the measurement-object gas flow cavity 15 is formed has a high temperature (e.g., about 800° C.). The part having the high temperature is arranged to be accommodated in the inner protection cover 130 and be in contact with a measurement-object gas. The measurement-object gas reaching in the vicinity of the sensor element 101 is heated by the sensor element 101 having high temperature to become at high temperature. Therefore, when oxygen and hydrogen coexist in the measurement-object gas, a reaction between oxygen and hydrogen (namely, an oxidation reaction of hydrogen) may occur. The reaction between oxygen and hydrogen (namely, the oxidation reaction of hydrogen) is an exothermic reaction. When the local oxidation reaction of hydrogen occurs in the vicinity of the sensor element 101, the reaction heat is considered to generate thermal stress to the sensor element 101.

Since the front end part of the sensor element 101 in which the measurement-object gas flow cavity 15 is formed has the high temperature by the heater 72, a rapid oxidation reaction of hydrogen may be likely to occur especially on the front end part of the sensor element 101. When the local oxidation reaction of hydrogen rapidly occurs in the vicinity of the sensor element 101, it is concerned that a crack may occur in an internal structure of the sensor element 101 depending on the magnitude of the thermal stress generated at the time.

[Protection Cover]

Next, configuration of the protection cover of the present invention will be described in detail with reference to FIG. 1, and FIG. 3 to FIG. 8. As shown in FIG. 1, the gas sensor 100 of this embodiment includes the metal-made element protection cover 120 that protects the above-described front end part of the sensor element 101, namely, the part of the sensor element 101 in contact with the measurement-object gas. The element protection cover 120 has a plurality of penetrating holes to flow a gas, and is configured to supply a measurement-object gas to the front end part of the sensor element 101 through the penetrating holes.

In this embodiment, the element protection cover 120 includes the bottomed cylindrical inner protection cover 130 accommodating a part of the sensor element 101 including the one end (front end), and the bottomed cylindrical outer protection cover 140 disposed outside of the inner protection cover 130 and accommodating the inner protection cover 130. In this embodiment, the inner protection cover 130 corresponds to the protection cover of the present invention, and the outer protection cover 140 corresponds to the outer cover of the present invention.

The inner protection cover 130 is a bottomed cylindrical metal member that accommodates a part of the sensor element 101 including the one end (front end). The inner protection cover 130 is arranged so that an axial direction of the inner protection cover 130 coincides or substantially coincides with the longitudinal direction of the sensor element 101. The inner protection cover 130 has a bottom on the further front end side than the front end surface 101*a* of the sensor element 101. A space is present between the sensor element 101 and the inner protection cover 130 so that the measurement-object gas can flow. The inner protection cover 130 accommodates at least a part of the sensor element 101 to be in contact with the measurement-object gas. For example, the inner protection cover 130 may accommodate at least a part of the sensor element 101 from the front end surface 101*a* having the gas inlet 10 to a rear end of the outer pump electrode 23 in the longitudinal direction of the sensor element 101. Alternatively, the inner protection cover 130 may accommodate a part of the sensor element 101 in which the measurement-object gas flow cavity 15 is present. Further, the inner protection cover 130 may accommodate a part of the sensor element 101 from the front end surface 101*a* to a position of the reference electrode 42 or to a position rearward the reference electrode 42. Such a part accommodated in the inner protection cover 130 may be appropriately determined within a range where gastightness is maintained between the front end side of the sensor element 101 in contact with the measurement-object gas and the rear end side of the sensor element 101 in contact with the reference gas.

In this embodiment, the inner protection cover 130 includes a first member 131 and a second member 132. The first member 131 has a cylindrical large-diameter portion 131*a* fitted to a front end of an outer periphery of the housing 151, a cylindrical small-diameter portion 131*b* smaller in diameter than the large-diameter portion 131*a*, and a stepped portion 131*c* that connects the large-diameter portion 131*a* and the small-diameter portion 131*b*. The second member 132 has a cylindrical tubular portion 132*a* fitted to the small-diameter portion 131*b* of the first member 131, and a tapered bottom portion 132*b* continued to a front end of the tubular portion 132*a*. A rear end of the tubular portion 132*a* is deformed in a U-shape to form a gas diffusion piece 132*c*. Two principal surfaces (the top surface 101*c* and the bottom surface 101*d*), and two side surfaces (the left surface 101*e* and the right surface 101*f*) of the sensor element 101 are surrounded by a side surface of the inner protection cover 130 formed by the small-diameter portion 131*b* of the first member 131 and the tubular portion 132*a* of the second member 132. It is to be noted that the inner protection cover 130 may be a member in which the first member 131 and the second member 132 are integrally formed.

The inner protection cover 130 has an inner gas inflow hole H2 and an inner gas outflow hole H3. The inner gas inflow hole H2 is a hole (for example, a round hole) penetrating the side surface of the inner protection cover 130 that surrounds the sensor element 101. That is, the inner gas inflow hole H2 is formed on the side surface at a position where the sensor element 101 exists in the axial direction of the inner protection cover 130 (or, the longitudinal direction of the sensor element 101). Specifically, a plurality of the inner gas inflow holes H2 is formed on a circumference of the small-diameter portion 131*b* of the first member 131 at a position closer to the rear end than the second member 132.

The inner gas outflow hole H3 is a penetrating hole formed on a bottom of the inner protection cover 130. The inner gas outflow hole H3 is formed on a lowest bottom part of the bottom portion 132*b* of the second member 132. The inner gas outflow hole H3 may be located further forward than the front end surface 101*a* of the sensor element 101. For example, the inner gas outflow hole H3 may be located on a tapered side part of the bottom portion 132*b*. A shape of the bottom portion 132*b* may not be limited to a tapered shape such as a conical shape and a truncated conical shape, and may be a planar shape.

The outer protection cover 140 is a bottomed cylindrical metal member that is disposed outside the inner protection cover 130 and accommodates the inner protection cover 130. The outer protection cover 140 is arranged so that an axial direction of the outer protection cover 140 coincides or substantially coincides with the axial direction of the inner protection cover 130. The outer protection cover 140 has a bottom on the further front end side than the bottom portion 132*b* of the inner protection cover 130 (the second member 132). A space is present between the inner protection cover 130 and the outer protection cover 140 so that the measurement-object gas can flow. The outer protection cover 140 includes a cylindrical large-diameter portion 140*a* fitted to an outer periphery of the large-diameter portion 131*a* of the first member 131 in the inner protection cover 130 and the outer periphery of the housing 151, a cylindrical body portion 140*b* extending from the large-diameter portion 140*a* toward the front end side, a front end portion 140*c* formed on the front end side of the body portion 140*b* in a bottomed cylindrical shape that is smaller in diameter than the body portion 140*b* and has a bottom on the front end side, and a stepped portion 140*d* connecting the body portion 140*b* and the front end portion 140*c*. The front end portion 140*c* is fitted to the tubular portion 132*a* of the second member 132 in the inner protection cover 130. This fitting point separates a space between the body portion 140*b* of the outer protection cover 140 and the inner protection cover 130, and a space between the front end portion 140*c* of the outer protection cover 140 and the inner protection cover 130.

The outer protection cover 140 has an outer gas inflow hole H1 and an outer gas outflow hole H4. The outer gas inflow hole H1 is a penetrating hole formed at a position different from the inner gas inflow hole H2 and the inner gas outflow hole H3 of the inner protection cover 130 in the longitudinal direction of the sensor element 101 (or, the axial direction of the outer protection cover 140). A plurality of the outer gas inflow hole H1 is formed on a circumference of the body portion 140*b* of the outer protection cover 140 at a position closer to the front end than the gas diffusion piece 132*c* of the second member 132 of the inner protection cover 130. The outer gas outflow hole H4 is a penetrating hole formed at a position different from the inner gas inflow hole H2 and the inner gas outflow hole H3 of the inner protection cover 130 and the outer gas inflow hole H1 of the outer protection cover 140 in the longitudinal direction of the sensor element 101 (or, the axial direction of the outer protection cover 140). A plurality of the outer gas outflow hole H4 is formed on a circumference of the front end portion 140*c* of the outer protection cover 140 at a position closer to the front end than the inner gas outflow hole H3 of the inner protection cover 130. Alternatively, the outer gas outflow hole H4 may be formed on a bottom of the front end portion 140*c* in the outer protection cover 140. In this case, the outer gas outflow hole H4 may be arranged at a position different from the inner gas outflow hole H3 of the inner protection cover 130 in view of a plane including the bottom of the outer protection cover 140.

Figure 3:
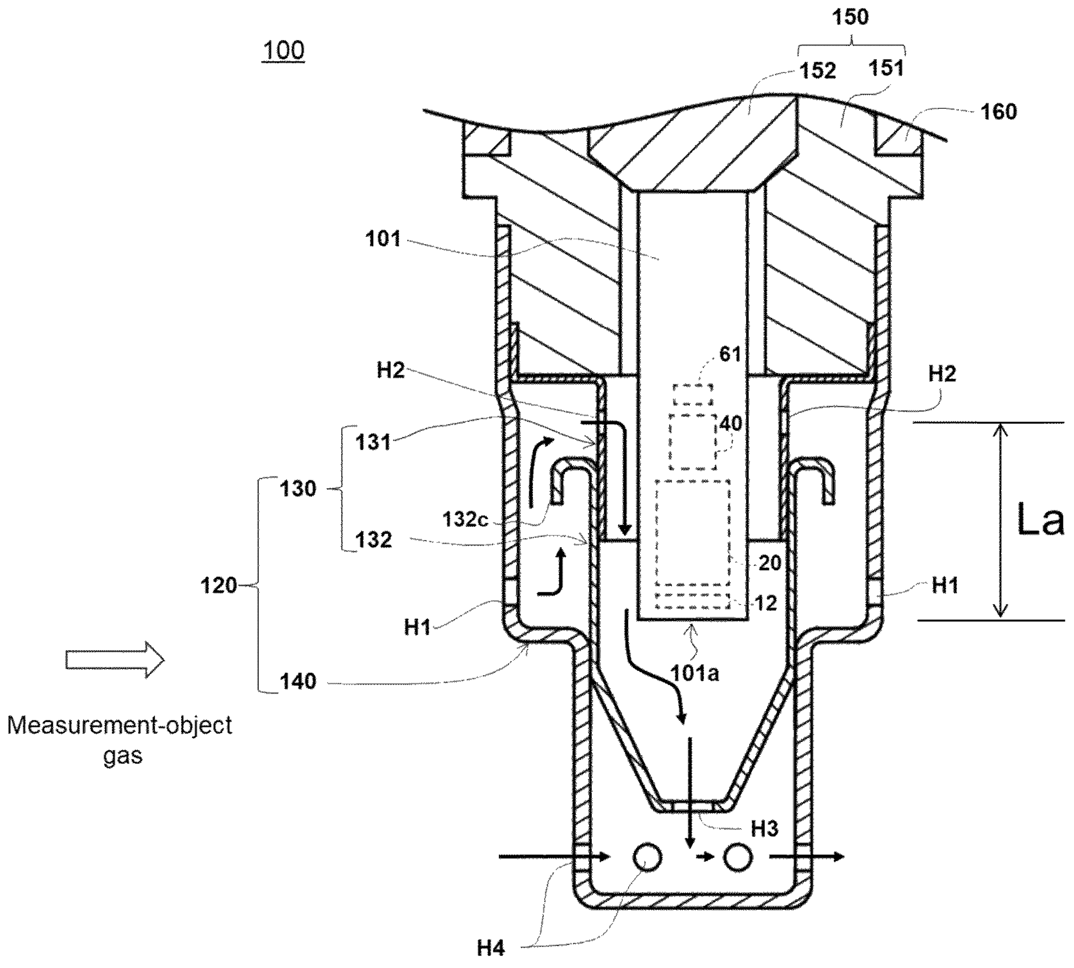
FIG. 3 is a schematic diagram showing flow of a measurement-object gas in an element protection cover 120 of the gas sensor 100.

FIG. 3 is a schematic diagram showing a flow of the measurement-object gas in the element protection cover 120, for example, when the gas sensor 100 is mounted on a pipe such as an exhaust pipe of an automobile and measures the measurement-object gas such as an exhaust gas. The flow of the measurement-object gas is schematically illustrated by an arrow, showing an example where the measurement-object gas flows from left to right in FIG. 3. The measurement-object gas flows into the outer protection cover 140 through the outer gas inflow hole H1. The measurement-object gas flowing in the outer protection cover 140 is diffused by the gas diffusion piece 132*c* of the second member 132 of the inner protection cover 130, and flows rearward. Then, the measurement-object gas flows into the inner protection cover 130 through the inner gas inflow hole H2 of the inner protection cover 130. The measurement-object gas flowing in the inner protection cover 130 flows along the sensor element 101 to the front end side and reaches the vicinity of the front end surface 101*a* of the sensor element 101. The measurement-object gas is introduced inside the sensor element 101 trough the gas inlet 10 on the front end surface 101*a*, and measurement of a target gas to be measured in the measurement-object gas is performed. The measurement-object gas is discharged from the vicinity of the front end surface 101*a* of the sensor element 101 to the outside of the element protection cover 120 via the inner gas outflow hole H3 of the inner protection cover 130 and the outer gas outflow hole H4 of the outer protection cover 140. Along with the flow of the measurement-object gas in the pipe, the measurement-object gas also flows into the outer protection cover 140 from an upstream outer gas outflow hole H4 (for example, the outer gas outflow hole H4 located on the left side in FIG. 3). The measurement-object gas discharged from the inner gas outflow hole H3 of the inner protection cover 130 is smoothly discharged to the outside from a downstream outer gas outflow hole H4 (for example, the outer gas outflow hole H4 located on the right side in FIG. 3) by the flow of the measurement-object gas entering from the upstream outer gas outflow hole H4. Actually, since each of the outer gas inflow hole H1, the inner gas inflow hole H2, the inner gas outflow hole H3, and the outer gas outflow hole H4 is formed in plurality, the measurement-object gas flows in and/or out thorough holes other than the holes indicated by the arrows, generally following the above-described flow of the measurement-object gas.

In the gas sensor 100 according to the present invention, the protection cover (in this embodiment, the inner protection cover 130) has the gas inflow hole (in this embodiment, the inner gas inflow hole H2) penetrating a side surface of the protection cover that surrounds the sensor element 101. And, this gas inflow hole is arranged so that each of parameters (a length ratio La/Lb, and gas oxidizing ability a in the sensor element 101) that will be described later is within a predetermined range.

Figure 4:
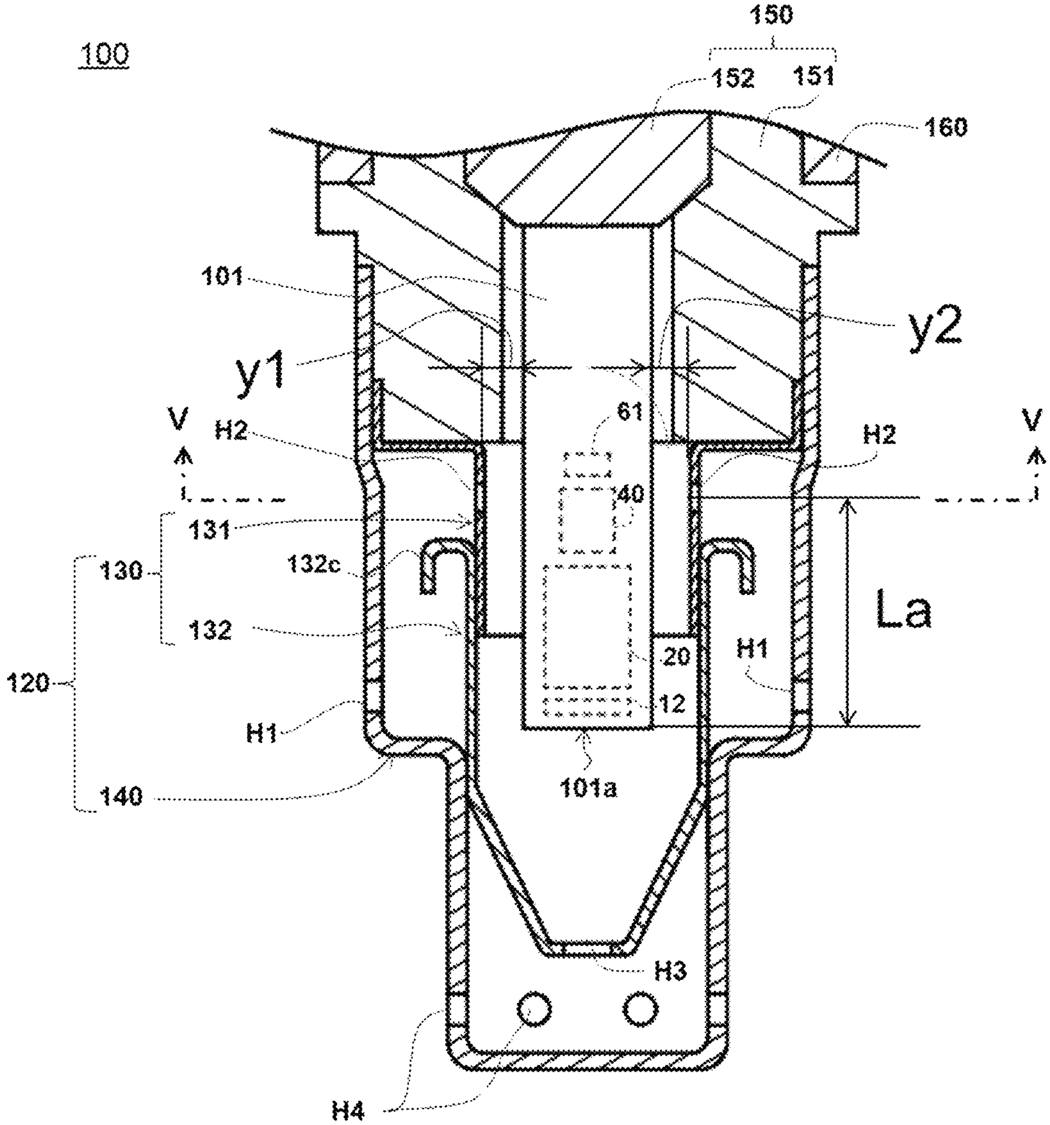
FIG. 4 is a partial sectional schematic view as the same as FIG. 1 for illustrating a length La.
Figure 5:
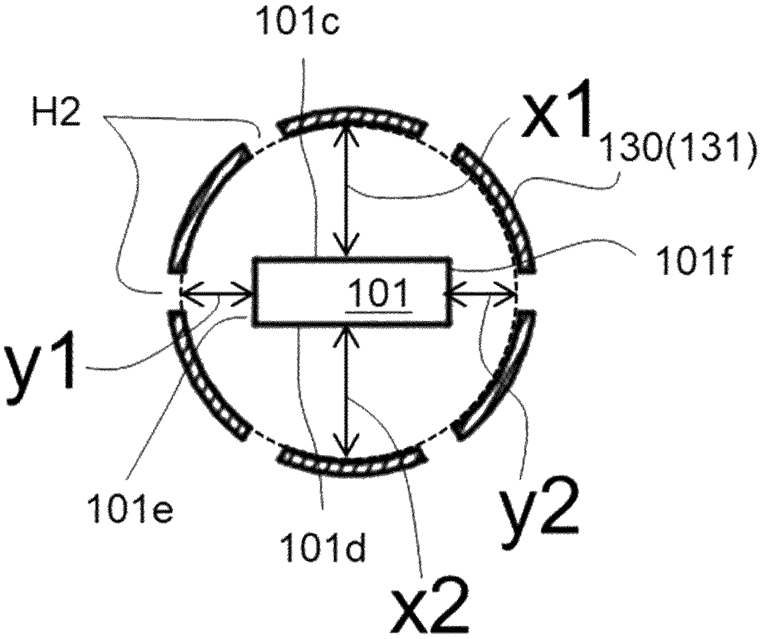
FIG. 5 is an enlarged partial sectional schematic view along a line V-V in FIG. 4, for illustrating a length index Lb.
Figure 6:
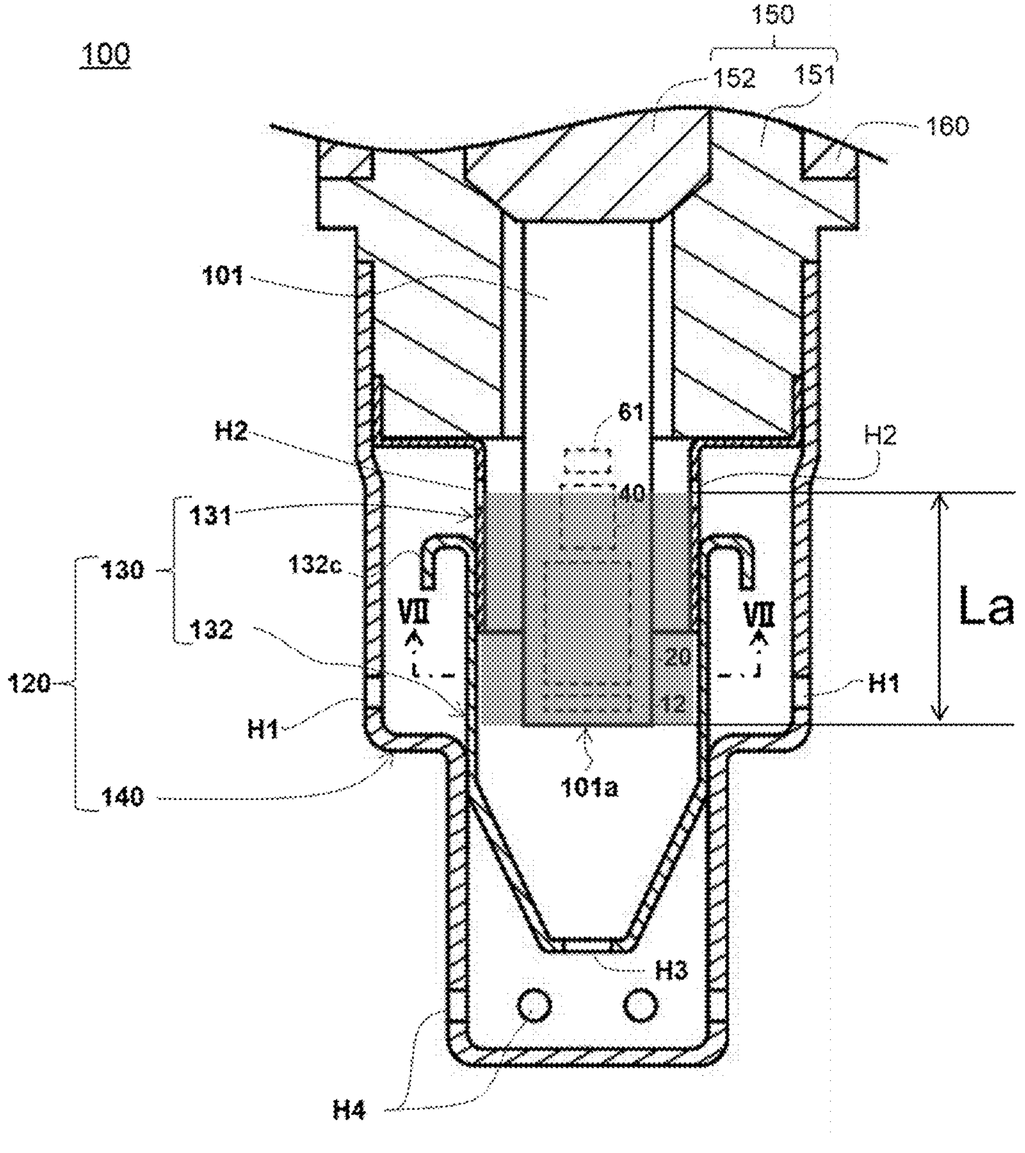
FIG. 6 is a partial sectional schematic view as the same as FIG. 1 for illustrating a volume V.
Figure 8:
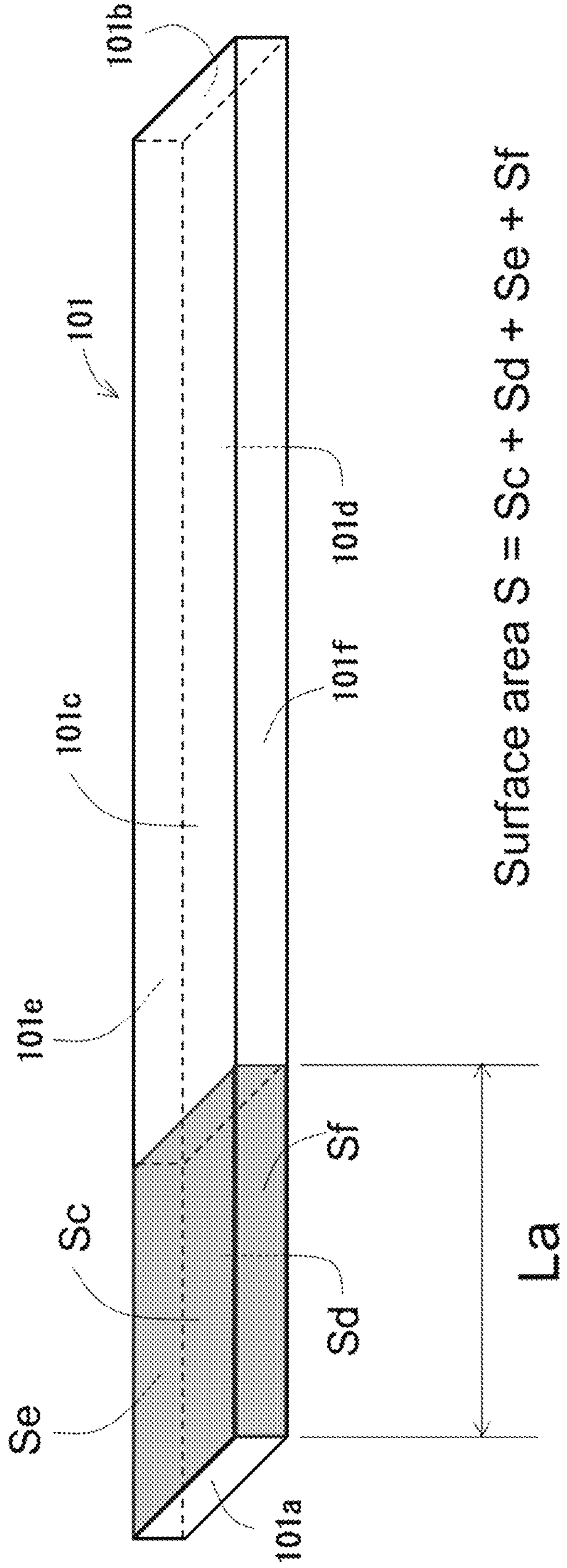
FIG. 8 is a perspective view of the sensor element 101, for illustrating the surface area S.

Detailed description will be done with reference to FIG. 4 to FIG. 8. FIG. 4 and FIG. 5 are schematic diagrams for illustrating a length La and a length index Lb. FIG. 4 is a partial sectional schematic view as the same as FIG. 1. FIG. 5 is an enlarged partial sectional schematic view along a line V-V in FIG. 4. In FIG. 5, illustration of an outer protection cover 140 is omitted. FIG. 6 to FIG. 8 are schematic diagrams for illustrating a surface area S and a volume V. FIG. 6 is a partial sectional schematic view as the same as FIG. 1. FIG. 7 is an enlarged partial sectional schematic view along a line VII-VII in FIG. 6. The VII-VII cross section is a cross section perpendicular to the longitudinal direction of the sensor element 101 at a position of the inner protection cover 130 (the second member 132) rearward of the front end of the sensor element 101. FIG. 8 is a perspective view of the sensor element 101. Illustration of confirmations such as electrodes in the element 101 is omitted.

As shown in FIG. 4, a length in the longitudinal direction of the sensor element 101 from the one end (the front end) of the sensor element 101 to a middle point of the gas inflow hole (the inner gas inflow hole H2) in the protection cover (the inner protection cover 130) in the longitudinal direction of the sensor element 101 is represented as a length La. As described above, the measurement-object gas flowing in the inner protection cover 130 through the inner gas inflow hole H2 flows along the sensor element 101 to the front end side and reaches the vicinity of the front end surface 101*a* of the sensor element 101. The length La indicates a flow path length in a flow path of the measurement-object gas flowing from the inner gas inflow hole H2 to the front end surface 101*a* of the sensor element 101 in the longitudinal direction of the sensor element 101.

The cross section shown in FIG. 5 is a cross section perpendicular to the longitudinal direction of the sensor element 101 at a center position of the inner gas inflow hole H2 of the inner protection cover 130 (the first member 131) in the longitudinal direction of the sensor element 101. In this embodiment, the six inner gas inflow holes H2 of the inner protection cover 130 are arranged equally on the circumference as shown in FIG. 5. However, the number of the inner gas inflow holes H2, positional relation between the inner gas inflow holes H2 and the sensor element 101, and the like are not limited to this. In the cross section in FIG. 5, an inner surface of the inner protection cover 130 is in a round shape. The round shape includes a circle, an ellipse, a circle that is at least partially distorted, or the like. In each position on in the axial direction of the inner protection cover 130, a cross section may have the same or different shape in comparison with the cross section shown in FIG. 5. The inner protection cover 130 may be in a substantially cylindrical shape, as in the case of this embodiment, in an area where the sensor element 101 is present in the axial direction. Alternatively, the inner protection cover 130 may be in a tapered shape or an inverse tapered shape, or may have a part having a different inner diameter. Alternatively, the inner protection cover 130 may have a part in a polygonal shape such as a triangle and a rectangle.

Description is made regarding an index of a length between the sensor element 101 and a circle determined by an inner surface of the protection cover (the inner protection cover 130), in a plane including the middle point of the gas inflow hole (the inner gas inflow hole H2) of the protection cover (the inner protection cover 130) in the longitudinal direction of the sensor element 101 and perpendicular to the longitudinal direction of the sensor element 101, that is, in a plane of the paper in FIG. 5. A longest distance between each of two principal surfaces and circumference of the circle determined by the inner surface of the inner protection cover 130 (the first member 131) facing the each of the two principal surfaces of the sensor element 101 is represented as a length x1 or a length x2. A longest distance between each of two side surfaces of the sensor element 101 and circumference of the circle facing the each of the two side surfaces is represented as a length y1 or a length y2.

That is, the length x1 represents a longest distance between the top surface 101*c* and the circumference facing the top surface 101*c* (an upper portion of the circumference in FIG. 5) of the circle (a circle shown by a dashed line in FIG. 5) determined by the inner surface of the inner protection cover 130. Here, the longest distance means the longest of lengths (distances) of perpendicular lines when each of the perpendicular lines from each position on the top surface 101*c* is extended to the circumference of the circle (the same shall apply hereinafter). The length x2 represents a longest distance between the bottom surface 101*d* and the circumference facing the bottom surface 101*d* (a lower portion of the circumference in FIG. 5) of the circle (the circle shown by the dashed line in FIG. 5) determined by the inner surface of the inner protection cover 130. The length y1 represents a longest distance between the left surface 101*e* and the circumference facing the left surface 101*e* (a left portion of the circumference in FIG. 5) of the circle (the circle shown by the dashed line in FIG. 5) determined by the inner surface of the inner protection cover 130. The length y2 represents a longest distance between the right surface 101*f* and the circumference facing the right surface 101*f* (a right portion of the circumference in FIG. 5) of the circle (the circle shown by the dashed line in FIG. 5) determined by the inner surface of the inner protection cover 130.

By using each of the length x1, x2, y1, and y2, an index of a length between the sensor element 101 and the circle determined by the inner surface of the inner protection cover 130 is represented as a length index:

$$Lb=(x1+x2+y1+y2)/4.$$

The length index Lb is an index that indicates a length (a length in a short length direction of the sensor element 101) of a gap between the sensor element 101 and the inner protection cover 130 of a flow path cross section, in the flow path of the measurement-object gas flowing from the inner gas inflow hole H2 to the front end surface 101*a* of the sensor element 101 in the longitudinal direction of the sensor element 101. The length index Lb is generally considered to be an index indicating size of the flow path cross section. The sensor element 101 is in the elongated plate shape that is substantially a rectangular parallelepiped. And, the inner protection cover 130 is substantially in the cylindrical shape on a region of the length La in the longitudinal direction of the sensor element 101. Therefore, in this embodiment, it is considered that the size of the flow path cross section is substantially the same over a whole of the region of the length La.

In this embodiment, as shown in FIG. 5, the sensor element 101 is arranged at a center of the circle (the circle shown by the dashed line in FIG. 5) determined by the inner surface of the inner protection cover 130. In this case, the length x1 and the length x2 are equal, and the length y1 and the length y2 are equal. When these relations are represented by x1=x2=x, and y1=y2=y, the length index Lb is represented as:

$$\text{the length index } Lb=(x+y)/2.$$

A ratio of the length La in the longitudinal direction of the sensor element 101 to the length index Lb in the short length direction of the sensor element 101 is represented as a length ratio La/Lb. The length ratio La/Lb is an index that indicates a degree to which the measurement-object gas flowing into the inner protection cover 130 is in contact with or passes near the surface of the sensor element 101 before reaching the front end surface 101*a* of the sensor element 101. It is considered that the larger the length ratio La/Lb, the more likely the measurement-object gas flowing into the inner protection cover 130 is to be in contact with at least any one of the two principal surfaces (the top surface 101*c* and the bottom surface 101*d*), and the two side surfaces (the left surface 101*e* and the right surface 101*f*) of the sensor element 101.

Sum of the respective surface areas of the two principal surfaces (the top surface 101*c* and the bottom surface 101*d*), and the two side surfaces (the left surface 101*e* and the right surface 101*f*) of the sensor element 101 corresponding a portion of the length La in the longitudinal direction of the sensor element 101 is represented as a surface area S. The surface area S is a surface area of a region present in a shaded portion in FIG. 6. That is, refering to FIG. 8, when surface areas S of respective portions of the length La from the front end surface 101*a* in the top surface 101*c*, the bottom surface 101*d*, the left surface 101*e* and the right surface 101*f* are respectively represented as Sc, Sd, Se, and Sf, the surface area S is:

$$S=Sc+Sd+Se+Sf.$$

The surface area S is a surface area of the sensor element 101 with which the measurement-object gas is to be in contact, in the flow path of the measurement-object gas flowing from the inner gas inflow hole H2 to the front end surface 101*a* of the sensor element 101 in the longitudinal direction of the sensor element 101.

As shown in FIG. 6 and FIG. 7, a volume of space (space of the shaded portion in FIG. 6 and FIG. 7. This space is referred to as a measurement-object gas existing space) in the protection cover (the inner protection cover 130) existing corresponding to the portion of the length La in the longitudinal direction of the sensor element 101 is represented as a volume V. The volume V indicates a total volume of the flow path of the measurement-object gas flowing from the inner gas inflow hole H2 to the front end surface 101*a* of the sensor element 101 in the longitudinal direction of the sensor element 101. In this embodiment, the volume Vis approximately obtained by subtracting the volume of the plate-shape sensor element 101 corresponding to the portion of the length La from the volume of a cylindrical shape portoion of the length La where the cross section is the circle determined by the inner surface of the side surface in the inner protection cover 130.

A ratio of the surface area S to the volume V is represented as a ratio S/V. The ratio S/V indicates a ratio, relative to the volume of the measurement-object gas inside the inner protection cover 130, of the surface area with which the measurement-object gas can be in contact, in the flow path of the measurement-object gas flowing from the inner gas inflow hole H2 to the front end surface 101*a* of the sensor element 101 in the longitudinal direction of the sensor element 101. As described above, in the vicinity of the surface of the sensor element 101 having high temperature, since the measurement-object gas reaching becomes at high temperature and a reaction between oxygen and hydrogen in the measurement-object gas is considered to occur, the larger the surface area of the sensor element 101 with respect to the volume of the measurement-object gas, that is, the larger the ratio S/V, the more hydrogen in the measurement-object gas can react with oxygen on the surface of the sensor element 101. In other words, the larger the ratio S/V, the higher the gas oxidizing ability on the surface of the sensor element 101. The ratio S/V is also referred as to gas oxidizing ability $\alpha$. Namely, $\alpha$=S/V.

As described above, since the sensor element 101 has high temperature, it is considered that when the measurement-object gas in which oxygen and hydrogen coexist is in contact with or passes near the surface of the sensor element 101, the measurement-object gas is heated to high temperature to cause a rapid reaction between oxygen and hydrogen (namely, an oxidation reaction of hydrogen). When the measurement-object gas is heated to high temperature in the vicinity of the two principal surfaces (the top surface 101*c* and the bottom surface 101*d*), and the two side surfaces (the left surface 101*e* and the right surface 101*f*) of the sensor element 101, the reaction between hydrogen and oxygen may occur in the vicinity of the two principal surfaces and the two side surfaces to consume hydrogen in the measurement-object gas, and therefore an amount of unreacted hydrogen may be reduced. Then, the measurement-object gas in which the amount of the unreacted hydrogen has been reduced reaches the gas inlet 10 that is open to the front end surface 101*a* of the sensor element 101.

In the gas sensor of the present invention, the length ratio La/Lb of the length La to the length index Lb is 0.9 or more, and the ratio S/V of the surface area S to the volume V is 0.15 $mm^{-1}$ or more. When the length ratio La/Lb and the ratio S/V are in such ranges, the surface area of the sensor element 101 for oxidizing hydrogen in the measurement-object gas flowing into the inner protection cover 130 can be secured even if the measurement-object gas in which oxygen and hydrogen coexist flows into the inner protection cover 130. Thus, hydrogen can be effectively oxidized on the two principal surfaces and the two side surfaces of the sensor element 101. It is considered that hydrogen can be averagely oxidized on a portion of the length La from the front end surface 101*a* of the two principal surfaces and the two side surfaces of the sensor element 101, and that the local oxidation reaction of hydrogen can be suppressed. The suppression of the local oxidation reaction of hydrogen can prevent generation of large local thermal stress. Therefore, even when the gas sensor 100 measures the measurement-object gas in which oxygen and hydrogen coexist, it is considered that a crack in the internal structure of the sensor element 101 does not occur and NOx concentration can be measured with high accuracy. Further, no opening is present on the two principal surfaces and the two side surfaces of the sensor element 101, and therefore the structural strength is considered to be relatively high in comparison with a region near the gas inlet 10 of the sensor element 101. By effectively oxidizing hydrogen in the measurement-object gas in the two principal surfaces and the two side surfaces of the sensor element 101, a concentration of hydrogen in the measurement-object gas reaching the gas inlet 10 on the front end surface 101*a* of the sensor element 101 can be sufficiently reduced. This further suppress the oxidation reaction of hydrogen in the vicinity of the gas inlet 10, and occurrence of the thermal stress caused by the reaction heat can be further reduced. Accordingly, it is considered that the occurrence of cracking in the sensor element 101 can be further decreased.

As described above, the length ratio La/Lb is 0.9 or more. Alternatively, the length ratio La/Lb may be, for example, 1.0 or more, 1.2 or more, 1.5 or more, 2.0 or more, or the like. An upper limit of the length ratio La/Lb is not particularly limited, and may be appropriately determined considering use environment or intended use of the gas sensor 100, performance required for the gas sensor 100 such as response that will be described later, and the like. The length ratio La/Lb may be, for example, 7 or less, 5 or less, or the like.

As described above, the gas oxidizing ability $\alpha$ (=the ratio S/V) of the sensor element 101 is 0.15 $mm^{-1}$ or more. Alternatively, the gas oxidizing ability $\alpha$ (=the ratio S/V) may be, for example, 0.18 $mm^{-1}$ or more, 0.2 $mm^{-1}$ or more, 0.25 $mm^{-1}$ or more, or the like. An upper limit of the gas oxidizing ability a is not particularly limited, and may be appropriately determined considering use environment or intended use of the gas sensor 100, performance required for the gas sensor 100 such as response that will be described later, and the like. The gas oxidizing ability a may be, for example, 0.5 $mm^{-1}$ or less, 0.4 $mm^{-1}$ or less, or the like.

Even if the length ratio La/Lb is 0.9 or more, when the gas oxidizing ability $\alpha$ (=the ratio S/V) is extremely small, the surface area of the sensor element 101 is extremely small relative to the volume of the measurement-object gas, and therefore it is concerned that hydrogen in the measurement-object gas may not be sufficiently oxidized. Even if the gas oxidizing ability $\alpha$ (=the ratio S/V) is 0.15 $mm^{-1}$ or more, when the length ratio La/Lb is extremely small, the flow path of the measurement-object gas flowing from the inner gas inflow hole H2 to the front end surface 101*a* of the sensor element 101 in the longitudinal direction of the sensor element 101 is so short that the measurement-object gas cannot be sufficiently in contact with or cannot sufficiently pass near the surface of the sensor element 101, and therefore it is concerned that hydrogen in the measurement-object gas may not be sufficiently oxidized. Accordingly, it is preferred that the length ratio La/Lb is 0.9 or more and the gas oxidizing ability $\alpha$ (=the ratio S/V) is 0.15 $mm^{-1}$ or more.

For example, when a concentration of a target gas to be measured in a measurement-object gas momently changes, as when the gas sensor 100 is used for measurement of an exhaust gas from a hydrogen engine vehicle, it is required that a response of a concentration output value in the gas sensor 100 to change of NOx concentration in the measurement-object gas is good. For example, the shorter a time required from a time point when NOx concentration in the measurement-object gas flowing outside the gas sensor 100 until a time point when the pump current Ip2 flowing through the measurement pump cell 41 becomes a current value corresponding to NOx concentration after the change, the better the response is. The measurement-object gas in which NOx concentration has changed flow into the element protection cover 120, reaches the gas inlet 10 of the sensor element 101, and is introduced inside the sensor element 101 to reach the measurement electrode 44, and then the pump current Ip2 flowing through the measurement pump cell 41 becomes a current value corresponding to NOx concentration after the change. Thus, the faster the measurement-object gas in the element protection cover 120 is replaced, the better the response can be obtained.

As described above, the length La indicates the flow path length in the flow path of the measurement-object gas flowing from the inner gas inflow hole H2 to the front end surface 101*a* of the sensor element 101 in the longitudinal direction of the sensor element 101. When the flow path length is short, the measurement-object gas in the inner protection cover 130 tends to be replaced more quickly. The length La may vary depending on responsiveness required for the gas sensor 100 or the configuration of the gas sensor, and may be, for example, 10 mm or less. When the length La is within such a range, it is considered that good responsiveness can be maintained. Alternatively, the length La may be, for example, 9 mm or less, 7 mm or less, 4 mm or less, or the like. A lower limit of the length La is not particularly limited with respect to the responsiveness, and the length La may be appropriately determined considering the length ratio La/Lb and the gas oxidizing ability α (=the ratio S/V) that are described above.

The gas sensor 100 for detecting the NOx concentration in a measurement-object gas has been described above as an example of the embodiment according to the present invention, but the present invention is not limited to this embodiment. The present invention may include various gas sensors different in configuration as long as the object of the present invention is achieved, that is, as long as a target gas to be measured in a measurement-object gas is accurately measured by suppressing the occurrence of cracking in a sensor element even when a gas containing gas species that can cause an exothermic reaction, such as a gas in which oxygen and hydrogen coexist, is introduced into the gas sensor as the measurement-object gas.

In the above embodiment, the gas sensor 100 detects the NOx concentration in a measurement-object gas. However, the target gas to be measured is not limited to NOx. For example, the target gas to be measured may be oxygen $O_2$, or an oxide gas other than NOx (e.g., carbon dioxide $CO_2$, water $H_2O$). Alternatively, the target gas to be measured may be a non-oxide gas such as ammonia $NH_3$. When the target gas to be measured is a non-oxide gas, the non-oxide gas is converted to an oxide gas (for example, in the case of ammonia $NH_3$, $NH_3$ is converted to NO), and a measurement-object gas containing the converted oxide gas is introduced into the third internal cavity 61. At the measurement electrode 44, the converted oxide gas in the measurement-object gas is reduced so that oxygen is generated. The target gas to be measured can be detected by acquiring the generated oxygen as the pump current Ip2 in the measurement pump cell 41. The conversion from the non-oxide gas to the oxide gas can be performed by allowing at least one of the inner main pump electrode 22 and the auxiliary pump electrode 51 to function as a catalyst.

The gas sensor may be capable of measuring two or more kinds of target gases to be measured. For example, the gas sensor may detect a concentration of nitrogen oxide NOx when the measurement-object gas is in a lean atmosphere, and may detect a concentration of ammonia $NH_3$ when the measurement-object gas is in a rich atmosphere. For example, the gas sensor may determine whether the measurement-object gas is in the lean atmosphere or in the rich atmosphere on the basis of the electromotive force (the voltage Vref) generated in the sensor cell 83, and may detect NOx concentration on the basis of the pump current flowing through the measurement pump cell 41, as described above, when the measurement-object gas is in the lean atmosphere. When the measurement-object gas is in the rich atmosphere, ammonia $NH_3$ may be converted to NO in at least one of the inner main pump electrode 22 and the auxiliary pump electrode 51, and $NH_3$ concentration may be detected on the basis of the pump current flowing through the measurement pump cell 41. Such a gas sensor is effective in the case of using downstream of a so-called three-way catalyst (TWC).

In the above embodiment, the element protection cover 120 is a cover with a doble structure having the inner protection cover 130 and the outer protection cover 140. However, the element protection cover is not limited to this. The inner protection cover 130 that is arranged on the nearest position to the sensor element 101 may be configured to satisfy the length ratio La/Lb and the gas oxidizing ability α (=the ratio S/V) of the present invention. The position, shape, size, number and the like of each of the inner gas inflow hole H2 and the inner gas outflow hole H3 in the inner protection cover 130 may be appropriately determined. For example, the shape of the inner gas inflow hole H2 may be a circle, an elliptical shape, a rectangle shape, or various other shapes. For example, a straightening piece may be formed in the vicinity of the penetrating hole of the inner gas inflow hole H2. Presence or absence of the gas diffusion piece 132*c* of the inner protection cover 130, and the shape of the gas diffusion piece 132*c*, if formed, may be appropriately determined. The position, shape, size, number and the like of each of the outer gas inflow hole and the outer gas outflow hole in the outer protection cover 140 may also be appropriately determined. Other shapes, a plate thickness, and the like of the inner protection cover 130 and the outer protection cover 140 may be appropriately determined. The element protection cover 120 may have a single structure (that is, only the protection cover of the present invention), or may have a triple structure (for example, a structure further having a middle cover in addition to the protection cover and the outer cover of the present invention). The structure of the element protection cover 120 may be appropriately determined considering use conditions (such as flow speed and temperature of the measurement-object gas, and possibility of water splash due to a condensed water).

In the above embodiment, the sensor element 101 has such a structure that the oxygen-ion-conductive solid electrolyte layers are layered. However, a part of the sensor element 101 that does not constitute the respective pump cells and the respective sensor cells may not be formed of the solid electrolyte, and may be formed of other ceramics such as alumina.

In the above embodiment, the sensor element 101 has an opening (namely, the gas inlet 10) on the front end surface 101*a*, and is so configured that the measurement-object gas is introduced inside the sensor element 101 from the opening on the front end surface 101*a*. However, the sensor element 101 is not limited to this. For example, the measurement-object gas flow cavity 15 may be so configured that the measurement-object gas is introduced from a side surface along the longitudinal direction of the sensor element 101 (the base part 102) near the front end. For example, the measurement-object gas flow cavity 15 may have an opening that communicates with the buffer space 12 or a position near the buffer space 12 of the first internal cavity 20, on the side surface along the longitudinal direction of the base part 102. In this case, the measurement-object gas is introduced from the side surface along the longitudinal direction of the base part 102 through the opening.

Also, in the case where the sensor element has an opening on the side surface near the front end, by configuring the positional relation between the sensor element 101 and the inner protection cover 130 to satisfy the length ratio La/Lb and the ratio S/V of the present invention, it is considered, as with the case of the above embodiment, that hydrogen can be averagely oxidized on a portion of the length La from the front end surface 101*a* of the two principal surfaces and the two side surfaces of the sensor element 101, and that the local oxidation reaction of hydrogen can be suppressed. Therefore, as with the case of the above embodiment, it is considered that the occurrence of cracking in the sensor element 101 can be decreased.

In the gas sensor 100 of the above embodiment, as shown in FIG. 2, the sensor element 101 has a structure in which three internal cavities, the first internal cavity 20, the second internal cavity 40, and the third internal cavity 61 are provided and the inner main pump electrode 22, the auxiliary pump electrode 51, and the measurement electrode 44 are respectively disposed in these internal cavities. However, the structure of the sensor element 101 is not limited thereto. For example, the sensor element 101 may have a structure in which two internal cavities, the first internal cavity 20 and the second internal cavity 40 are provided, the inner main pump electrode 22 is disposed in the first internal cavity 20, and the auxiliary pump electrode 51 and the measurement electrode 44 are disposed in the second internal cavity 40. In this case, for example, a porous protective layer covering the measurement electrode 44 may be formed as a diffusion-rate limiting part between the auxiliary pump electrode 51 and the measurement electrode 44.

Each of the components of the sensor element 101 other than the above-described components of the internal cavities, such as the measurement-object gas flow cavity 15 and the electrodes, can also be variously embodied in accordance with the kind of target gas to be measured, the intended use or use environment of the gas sensor and the like.

The gas sensor 100 of the above embodiment is a so-called limiting current type gas sensor that detects a concentration of a target gas to be measured on the basis of the pump current Ip2 flowing through the measurement pomp cell 41. However, the gas sensor is not limited thereto. The gas sensor may be a so-called mixed potential type gas sensor that detects a concentration of a target gas to be measured on the basis of a potential difference between an electrode in contact with a measurement-object gas and a reference electrode in contact with a reference gas.

EXAMPLES

Hereinafter, the case of actually manufacturing a gas sensor and conducting a test is described as Examples. The present invention is not limited to the following Examples.

Examples 1 to 5 and Comparative Examples 1 to 3

Regarding the gas sensor 100 shown in FIGS. 1 and 2, gas sensors in which each of parameters: a length La [mm], a length ratio La/Lb, and a gas oxidizing ability $\alpha$=S/V [$mm^{-1}$] of the sensor element 101 was different from each other were manufactured as Examples 1 to 5 and Comparative Examples 1 to 3.

The value of each of the parameters in each of Examples 1 to 5 and Comparative Examples 1 to 3 was as follows.

In Example 1, La=7.1 mm, La/Lb=3.3, and $\alpha$=0.3 $mm^{-1}$.

In Example 2, La=4 mm, La/Lb=3.3, and $\alpha$=0.3 $mm^{-1}$.

In Example 3, La=10 mm, La/Lb=2.3, and $\alpha$=0.2 $mm^{-1}$.

In Example 4, La=10 mm, La/Lb=0.9, and $\alpha$=0.15 $mm^{-1}$.

In Example 5, La=14 mm, La/Lb=3.3, and $\alpha$=0.3 $mm^{-1}$.

In Comparative Example 1, La=0.6 mm, La/Lb=0.2, and $\alpha$=0.1 $mm^{-1}$.

In Comparative Example 2, La=10 mm, La/Lb=0.6, and $\alpha$=0.15 $mm^{-1}$.

In Comparative Example 3, La=10 mm, La/Lb=0.9, and $\alpha$=0.1 $mm^{-1}$.

Each of the gas sensors of Examples 1 to 5 and Comparative Examples 1 to 3 was manufactured so as to have a desired length ratio La/Lb, a desired gas oxidizing ability $\alpha$=S/V in the sensor element 101, and a desired length La, by changing a position of the inner gas inflow hole H2 in the inner protection cover 130 in the longitudinal direction of the sensor element, and an inner diameter of the inner protection cover 130. In all of the gas sensors of Examples 1 to 5 and Comparative Examples 1 to 3, dimensions of the inner protection cover 130 other than the position of the inner gas inflow hole H2 in the inner protection cover 130 in the longitudinal direction of the sensor element, and the inner diameter of the inner protection cover 130 were the same. In all of the gas sensors of Examples 1 to 5 and Comparative Examples 1 to 3, the same sensor element 101 and the same outer protection cover were used.

[Evaluation on Cracking Risk]

Easiness of occurrence of cracking (a cracking risk) in the sensor element 101 was evaluated for each of the gas sensors of Examples 1 to 5 and Comparative Examples 1 to 3. Specifically, initially, the gas sensor 100 was attached to a testing piping, and was driven. That is, the heater 72 was energized to heat the sensor element 101, and the respective pump cells 21, 50 and 41, and the respective sensor cells 80, 81, 82 and 83 were actuated as described above. A driving temperature of the sensor element 101 was 840° C. In this state, a model gas containing oxygen and hydrogen was flowed to the testing piping. And, it was confirmed whether or not cracking occurred in the sensor element 101, when the gas sensor 100 in a driving state was exposed to the model gas for 100 seconds. The components of the model gas was oxygen $O_2$=5%, hydrogen $H_2$=1.8%, and the remainder was nitrogen $N_2$. Each of gas concentrations was in a unit of a volume basis (the same shall apply hereinafter).

Twelve gas sensors of each of Examples 1 to 5 and Comparative Examples 1 to 3 were prepared, and probability of occurrence of cracking (=the number of occurrence times of cracking/the number of test samples×100) [%] was calculated from the number of occurrence times of cracking in the twelve gas sensors. The probability of occurrence of cracking was judged according to the following criteria.

A+: Probability of occurrence of cracking is not more than 5%;

A: Probability of occurrence of cracking is more than 5% and not more than 15%;

A−: Probability of occurrence of cracking is more than 15% and not more than 30%; and B: Probability of occurrence of cracking is more than 30% and not more than 50%.

[Evaluation on Responsiveness]

Responsiveness of detection of NOx concentration was evaluated for each of the gas sensors of Examples 1 to 5 and Comparative Examples 1 to 3. Specifically, initially, the gas sensor 100 was attached to a testing piping, and was driven. That is, the heater 72 was energized to heat the sensor element 101, and the respective pump cells 21, 50 and 41, and the respective sensor cells 80, 81, 82 and 83 were actuated as described above. A driving temperature of the sensor element 101 was 840° C. When the gas sensor 100 is driven, the pump current Ip2 flowing through the measurement pump cell 41 flows in accordance with NOx concentration in a measurement-object gas.

In this state, the first model gas containing 0 ppm of NOx (the remainder was nitrogen $N_2$) was flowed to the testing piping as a measurement-object gas, and the pump current Ip2 was waited until it became stable. After the pump current Ip2 became stable, the measurement-object gas flowed to the test piping was switched to the second model gas containing 500 ppm of NOx (the remainder was nitrogen $N_2$). And, a temporal change in the pump current Ip2 was evaluated in the case where NOx concentration in the measurement-object gas was changed from 0 ppm to 500 ppm. Where the pump current Ip2 just before the NOx concentration in the measurement-object gas was changed (namely, just before the switching from the first model gas to the second model gas) was 0% and the pump current Ip2 at the time when the pump current Ip2 became stable after the pump current Ip2 varied due to a change of the NOx concentration was 100%, an elapsed time from when a value of the pump current Ip2 exceeds 10% to when the value of the pump current Ip2 exceeds 90% was defined as a response time [msec] of NOx concentration detection. It means that the responsiveness of NOx concentration detection in the sensor element 101 increases as the response time shortens.

The response time described above was calculated for each of the gas sensors of Examples 1 to 5 and Comparative Examples 1 to 3. The response time was judged according to the following criteria.

A: Response time is not more than 1200 msec;

B: Response time is more than 1200 msec and not more than 2000 msec; and

C: Response time is more than 2000 msec.

Table 1 shows the parameters and the evaluation results, in each of Examples 1 to 5 and Comparative Examples 1 to 3. Table 1 shows the value of each of the parameters (the length La, the length ratio La/Lb, and the gas oxidizing ability α=S/V of the sensor element 101) in each gas sensor, the evaluation result of the cracking risk, the evaluation result of the responsiveness, and the comprehensive evaluation. The comprehensive evaluation was based on the evaluation result of the cracking risk and took into account the evaluation result of the responsiveness.

TABLE 1

| | Parameters | | | Evaluation results | | |
|---|---|---|---|---|---|---|
| | La | La/Lb | α = S/V | Cracking risk | Responsiveness | Comprehensive evaluation |
| Example 1 | 7.1 | 3.3 | 0.3 | A+ | B | A+ |
| Example 2 | 4 | 3.3 | 0.3 | A+ | B | A+ |
| Example 3 | 10 | 2.3 | 0.2 | A | B | A |
| Example 4 | 10 | 0.9 | 0.15 | A− | B | A− |
| Example 5 | 14 | 3.3 | 0.3 | A+ | C | B |
| Comparative Example 1 | 0.6 | 0.2 | 0.1 | B | A | C |
| Comparative Example 2 | 10 | 0.6 | 0.15 | B | B | C |
| Comparative Example 3 | 10 | 0.9 | 0.1 | B | B | C |

It was confirmed that the cracking risk in each of the gas sensors of Example 1 to 5 was reduced compared to the gas sensors of Comparative Examples 1 to 3. It was confirmed that the larger value of the length ratio La/Lb, and the larger value of the gas oxidizing ability α=S/V of the sensor element 101 both were able to reduce the cracking risk.

In the gas sensors of Examples 1 to 5 and Comparative Examples 1 to 3, it was confirmed that the shorter the length La, the better the responsiveness. The gas sensor of Example 5 had the longest length La, and the response thereof was slightly slower than those of the gas sensors of Examples 1 to 4 and Comparative Examples 1 to 3. It is considered that a time required to replace the gas in the element protection cover 120 of Example 5 was slightly longer than those of other gas sensors, since the length La of Example 5 was long. If better responsiveness is required in light of the intended use and the use environment of the gas sensor 100, it may be advisable to set the length La to, for example, 10 mm or less, or the like.

The comprehensive evaluation was done on the basis of the evaluation result of the cracking risk and took into account the evaluation result of the responsiveness. All of the gas sensors can be used in actual use. However, when oxygen and hydrogen can coexist in the measurement-object gas, a gas sensor with the comprehensive evaluation of B or higher may be preferably used. It is more preferable to use a gas sensor with the comprehensive evaluation of A- or higher, since it can both reduce the cracking risk and provide good responsiveness.

As has been described above, according to the present invention, the occurrence of cracking in a sensor element can be suppressed even when a gas containing gas species that can cause an exothermic reaction, such as a gas in which oxygen and hydrogen coexist, is introduced into a gas sensor as the measurement-object gas, and thus a target gas to be measured in a measurement-object gas can be accurately measured.

EXPLANATION OF REFERENCE SIGNS IN THE DRAWINGS

10: gas inlet; 12: buffer space; 15: measurement-object gas flow cavity; 20: first internal cavity; 40: second internal cavity; 61: third internal cavity; 100: gas sensor; 101: sensor element; 101*a*: front end surface (of the sensor element); 101*b*: rear end surface (of the sensor element); 101*c*: top surface (of the sensor element); 101*d*: bottom surface (of the sensor element); 101*e*: left surface (of the sensor element); 101*f*: right surface (of the sensor element); 120: element protection cover; 130: inner protection cover; 131: first member (of the inner protection cover); 132: second member (of the inner protection cover); 132*c*: gas diffusion piece (of the second member of the inner protection cover); 140: outer protection cover; 150: element sealing body; 151: housing; 152: ceramic supporter; 160: fixing part; H1: outer gas inflow hole; H2: inner gas inflow hole; H3: inner gas outflow hole; H4: outer gas outflow hole.

What is claimed is:

1. A gas sensor for detecting a target gas to be measured in a measurement-object gas, the gas sensor comprising:

a sensor element in an elongated plate shape, including an oxygen-ion-conductive solid electrolyte layer, wherein a measurement-object gas flow cavity is formed on a side of one end in a longitudinal direction of the sensor element; and a protection cover in a bottomed cylindrical shape, accommodating a part of the sensor element that includes the one end in the longitudinal direction of the sensor element, wherein the protection cover has a gas inflow hole penetrating a side surface of the protection cover that surrounds the sensor element, and when a length in the longitudinal direction of the sensor element from the one end of the sensor element to a middle point in the longitudinal direction of the gas inflow hole of the protection cover is represented as a length La, and in a plane including the middle point in the longitudinal direction of the gas inflow hole of the protection cover and perpendicular to the longitudinal direction of the sensor element, a longest distance between each of two principal surfaces of the sensor element and circumference of a circle determined by an inner surface of the protection cover facing the each of the two principal surfaces is represented as a length x1 or a length x2, a longest distance between each of two side surfaces of the sensor element and circumference of the circle facing the each of the two side surfaces is represented as a length y1 or a length y2, and an index of a length between the sensor element and the circle determined by the inner surface of the protection cover is represented as a length index:

$$Lb=(x1+x2+y1+y2)/4,$$

a ratio La/Lb of the length La to the length index Lb is 0.9 or more, and when sum of respective surface areas of the two principal surfaces and the two side surfaces of the sensor element corresponding to a portion of the length La in the longitudinal direction is represented as a surface area S, and a volume of space in the protection cover existing corresponding to the portion of the length La in the longitudinal direction is represented as a volume V, a ratio S/V of the surface area S to the volume V is 0.15 $mm^{-1}$ or more.

2. The gas sensor according to claim 1, wherein the length La in the longitudinal direction is 10 mm or less.

3. The gas sensor according to claim 1, wherein the length x1 and the length x2 are x1=x2=x, the length y1 and the length y2 are y1=y2=y, and the length index Lb is represented as Lb=(x+y)/2.

4. The gas sensor according to claim 1, wherein the protection cover has a gas outflow hole on a bottom of the protection cover.

5. The gas sensor according to claim 1, wherein an outer cover is further disposed outside the protection cover and accommodates the protection cover, and the outer cover has an outer gas inflow hole at a position different from the gas inflow hole of the protection cover in the longitudinal direction of the sensor element.

6. The gas sensor according to claim 5, wherein the outer cover has an outer gas outflow hole at a position different from the gas inflow hole of the protection cover and the outer gas inflow hole of the outer cover in the longitudinal direction of the sensor element.

7. The gas sensor according to claim 1, wherein the measurement-object gas flow cavity of the sensor element has a gas inlet that is open to an end surface of the one end in the longitudinal direction of the sensor element.

* * * * *